US008413653B2

(12) United States Patent
Turiello

(10) Patent No.: US 8,413,653 B2
(45) **Date of Patent: *Apr. 9, 2013**

(54) SAFETY SYSTEM AND METHOD OF A TUNNEL STRUCTURE

(75) Inventor: Anthony J Turiello, Portola Valley, CA (US)

(73) Assignee: Rescue Air Systems, Inc., San Carlos, CA (US)

( * ) Notice: Subject to any disclaimer, the term of this patent is extended or adjusted under 35 U.S.C. 154(b) by 575 days.

This patent is subject to a terminal disclaimer.

(21) Appl. No.: 12/690,944

(22) Filed: Jan. 21, 2010

(65) Prior Publication Data

US 2010/0154922 A1 Jun. 24, 2010

Related U.S. Application Data

(63) Continuation-in-part of application No. 11/505,538, filed on Aug. 16, 2006, now Pat. No. 7,673,629.

(51) Int. Cl.

| | |
|---|---|
| *A61M 16/00* | (2006.01) |
| *A62B 9/00* | (2006.01) |
| *A62B 9/02* | (2006.01) |
| *E04D 13/18* | (2006.01) |

(52) U.S. Cl. ......... 128/204.21; 128/200.24; 128/204.18; 128/204.26; 128/205.22; 128/205.24; 52/173.3

(58) Field of Classification Search ............. 128/200.24, 128/201.24, 203.27, 204.18, 204.21, 205.26, 128/897, 898; 52/2.11–2.26, 169.6, 302.1–302.7, 52/173.1–173.3; 454/169–172; 137/377, 137/382; 62/78, 239, 640, 911; 169/44, 169/46; 220/88.1, 88.3

See application file for complete search history.

(56) References Cited

U.S. PATENT DOCUMENTS

| | | | | |
|---|---|---|---|---|
| 2,299,793 | A * | 10/1942 | Cannaday et al. | 128/202.13 |
| 3,973,562 | A * | 8/1976 | Jansson | 128/205.12 |
| 3,995,626 | A * | 12/1976 | Pearce, Jr. | 128/205.24 |
| 4,712,594 | A * | 12/1987 | Schneider | 141/114 |
| 4,862,931 | A * | 9/1989 | Vella | 141/1 |
| 5,570,685 | A * | 11/1996 | Turiello | 128/202.13 |
| 6,474,334 | B1 * | 11/2002 | Lemer | 128/204.18 |
| 6,502,421 | B2 * | 1/2003 | Kotliar | 62/640 |
| 6,688,309 | B2 * | 2/2004 | York | 128/205.22 |
| 6,701,923 | B2 * | 3/2004 | Cazenave et al. | 128/204.22 |

(Continued)

OTHER PUBLICATIONS

National Fire Protection Association; National Fire Protection Association Standards on Self Contained Breathing Apparatus for Fire Fighters 1981 Edition; May 19, 1981; Dallas,Texas, USA.

*Primary Examiner* — Annette Dixon
(74) *Attorney, Agent, or Firm* — Raj Abhyanker, P.C.

(57) ABSTRACT

A safety system and method of an air distribution system of a tunnel structure is disclosed. In one embodiment, the air distribution includes a supply unit installed on a particular wall of the first set of walls to facilitate delivery of breathable air from a source of compressed air to an emergency support system of the tunnel structure, a fill site interior to the tunnel structure to provide the breathable air to a breathable air apparatus at multiple locations of the tunnel structure, a secure chamber of the fill site as a safety shield that confines a possible rupture of an over-pressurized breathable air apparatus within the secure chamber, a distribution structure that is compatible with use with compressed air that facilitates dissemination of the breathable air of the source of compressed air to multiple locations of the tunnel structure.

19 Claims, 15 Drawing Sheets

U.S. PATENT DOCUMENTS

| | | | | |
|---|---|---|---|---|
| 6,948,498 | B2 * | 9/2005 | Cazenave et al. | 128/204.22 |
| 7,055,780 | B2 * | 6/2006 | Phillips | 244/118.5 |
| 7,168,428 | B1 * | 1/2007 | Zoha | 128/202.27 |
| 7,255,104 | B2 * | 8/2007 | Phillips | 128/204.22 |
| 7,527,056 | B2 * | 5/2009 | Turiello | 128/205.26 |
| 7,621,269 | B2 * | 11/2009 | Turiello | 128/204.21 |
| 7,673,629 | B2 * | 3/2010 | Turiello | 128/204.21 |
| 7,677,247 | B2 * | 3/2010 | Turiello | 128/205.26 |
| 7,694,678 | B2 * | 4/2010 | Turiello | 128/204.21 |
| 2006/0219842 | A1 * | 10/2006 | Shell et al. | 244/118.5 |
| 2009/0178675 | A1 * | 7/2009 | Turiello | 128/202.13 |

* cited by examiner

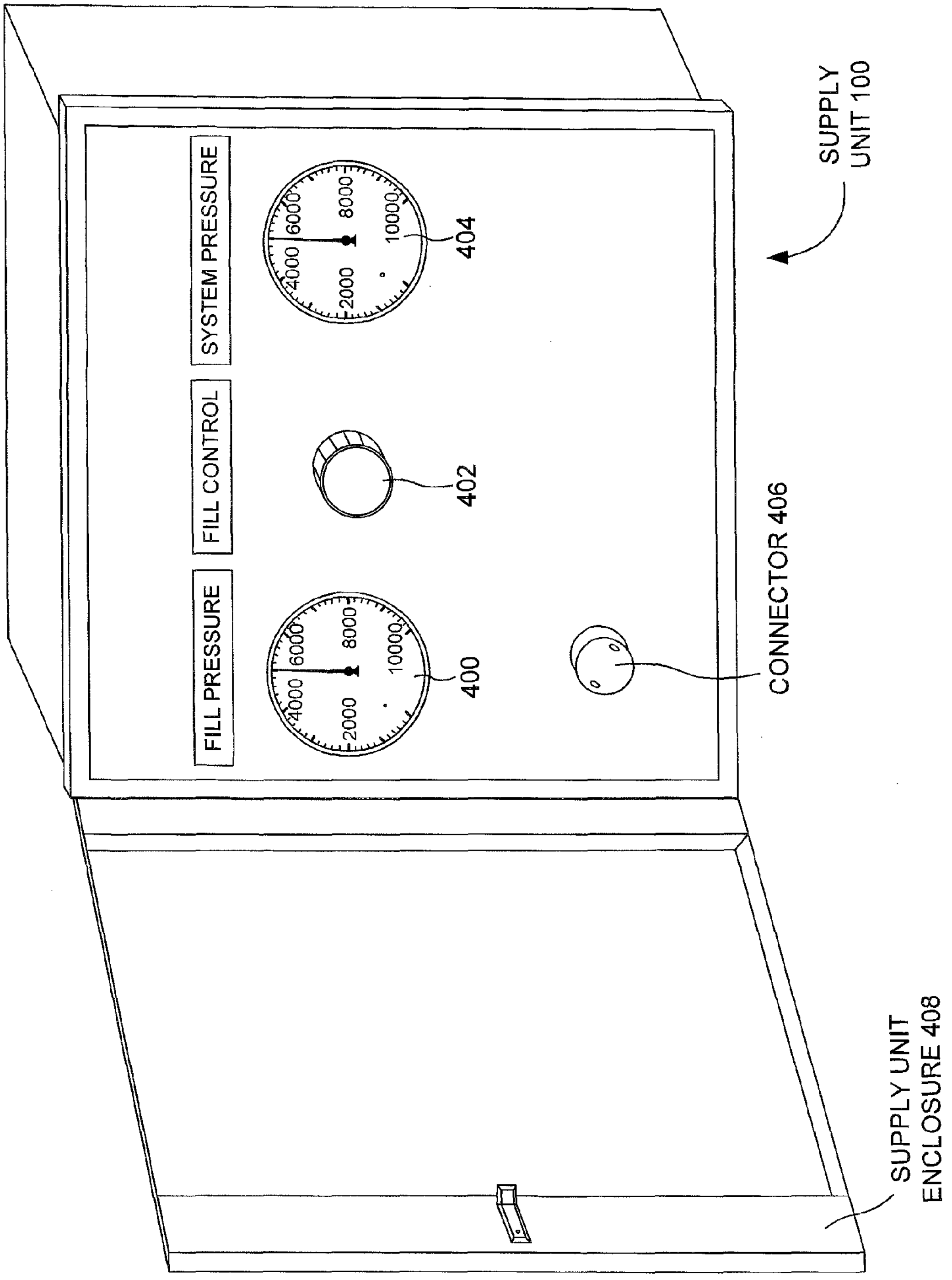
FIGURE 4A (FRONT VIEW)

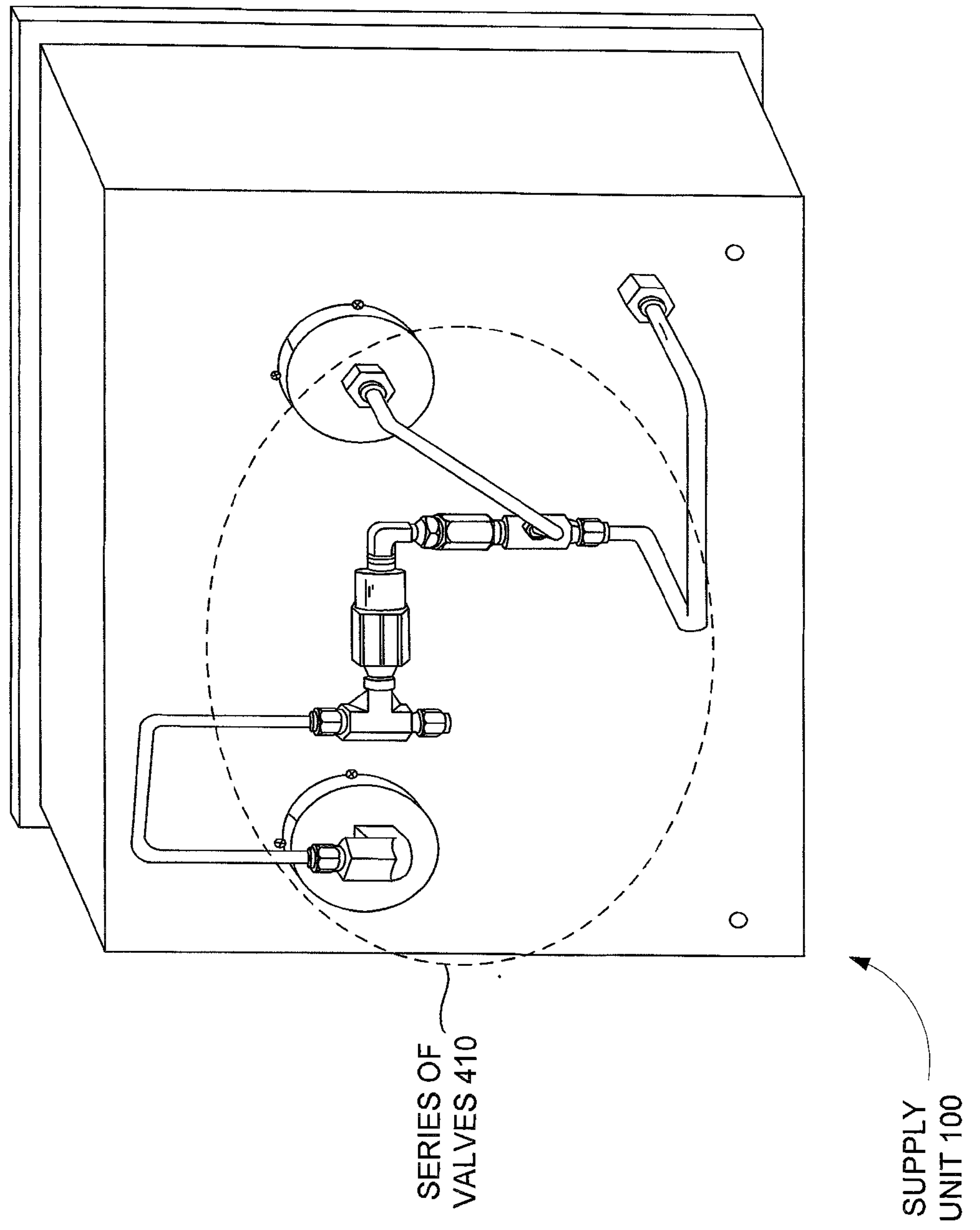
FIGURE 4B (REAR VIEW)

SAFETY SYSTEM AND METHOD OF A TUNNEL STRUCTURE

CLAIM OF PRIORITY

This is a Continuation-in-part application and claims priority from U.S. Utility application Ser. No. 11/505,538 titled "SAFETY SYSTEM AND METHOD OF A TUNNEL STRUCTURE" filed on Aug. 16, 2006, now U.S. Pat. No. 7,673,629 issued Mar. 9, 2010.

FIELD OF TECHNOLOGY

This disclosure relates generally to the technical fields of safety systems and, in one example embodiment, to a safety system and method of a tunnel structure.

BACKGROUND

A tunnel may be an artificial underground passage, (e.g. one built through a hill or under a tunnel, road, and/or river, etc.). The tunnel may be substantially horizontal and have a ratio of the length of the passage to the width of at least 2 to 1. In addition, the tunnel may be completely enclosed on all sides, and the openings may be saved for the length of the covered area causing limited accessibility to the tunnel. In a case of an emergency situation of a tunnel, emergency personnel may be deployed on-site of the structure to alleviate the emergency situation through mitigating a source of hazard as well as rescuing stranded civilians from the tunnel. The emergency situation may include events such as a fire, a chemical attack, tenor attack, subway accident, tunnel collapse, and/or a biological agent attack.

In such situations, breathing air inside the tunnel may be hazardously affected (e.g., depleted, absorbed, and/or contaminated). In addition, flow of fresh air into the tunnel may be significantly hindered due to the tunnel having enclosed regions, lack of windows, and/or high concentration of contaminants. As a result, inhaling air in the tunnel may be extremely detrimental and may further result in death (e.g., within minutes). Furthermore, emergency work may often need to be performed from within the tunnel (e.g., due to a limitation of emergency equipment able to be transported on a ground level).

The emergency personnel's ability to alleviate the emergency in an efficient manner may be adversely affected by the lack of breathing air and/or the abundance of contaminated air. A survival rate of stranded civilians in the tunnel may be substantially decreased due to a propagation of contaminated air throughout the tunnel placing a large number of innocent lives at significant risk.

As such, the emergency personnel may utilize a portable breathing air apparatus (e.g., self-contained breathing apparatus) as a source of breathing air during a rescue mission. However, the portable breathing air apparatus may be heavy (e.g., 20-30 pounds) and may only provide breathing air for a short while (e.g., approximately 15-30 minutes). In the emergency situation, the emergency personnel may need to walk and/or climb to a particular location within the structure to perform rescuing work due to inoperable transport systems (e.g. obstructed walkway, elevators, moving. sidewalks, and/or escalators, etc.). As such, by the time the emergency personnel reaches the particular location, his/her portable breathing air apparatus may have already depleted and may require running back to the ground floor for a new portable breathing air apparatus. As a result, precious lives may be lost due to precious time being lost.

An extra supply of portable breathing air apparatuses may be stored throughout the tunnel so that emergency personnel can replace their portable breathing air apparatuses within the tunnel. However, supplying structures with spare portable breathing air apparatuses may be expensive and take up space in the structure severely handicapping the ability of emergency personnel to perform rescue tasks. Furthermore, the tunnel may not regularly inspect the spare portable breathing air apparatuses. With time, the spare portable breathing air apparatuses may experience pressure loss placing the emergency personnel at significant risk when it is utilized in the emergency situation. The spare portable breathing air apparatuses may also be tampered with during storage. Contaminants may be introduced into the spare portable breathing air apparatuses that are detrimental to the emergency personnel

SUMMARY

A safety system and method of a tunnel structure are disclosed.

In one aspect, a safety system of a tunnel structure includes a supply unit of a tunnel structure to facilitate delivery of breathable air from a source of compressed air to an air distribution system of the tunnel structure, a valve to prevent leakage of the breathable air from the air distribution system potentially leading to loss of system pressure, a fill site interior to the tunnel structure to provide the breathable air to a breathable air apparatus at multiple locations of the tunnel structure, a distribution structure that is compatible with use with compressed air that facilitates dissemination of the breathable air of the source of compressed air to multiple locations of the tunnel structure.

The system may include a secure chamber of the fill station as a safety shield that confines a possible rupture of an over-pressurized breathable air apparatus within the secure chamber. The system my also include a secure chamber of the fill station as a safety shield that confines a possible rupture of an over-pressurized breathable air apparatus within the secure chamber. The system may also include an air storage sub-system to provide an additional supply of air to the tunnel structure in addition to the source of compressed air and an air storage tank of the air storage sub-system to provide storage of air that is dispersible to multiple locations of the tunnel structure. The air storage sub-system may also include a booster tank coupled to the air storage tank to store compressed air of a higher pressure than the compressed air that is stored in the air storage tank and a driving air source of the air storage sub-system to pneumatically drive a piston of a pressure booster to maintain a higher pressure of the air distribution system such that a breathable air apparatus is reliably filled. The system may also include an air monitoring system to automatically track and record any of impurities and contaminants in the breathable air of the air distribution system. The air monitoring system may also include an automatic shut down feature to suspend air dissemination to the tunnel structure in a case that any of impurity levels and contaminant levels exceed a safety threshold. The system may also include a pressure monitoring system to continuously track and record the system pressure of the air distribution system. Further, any of a CGA (Compressed Gas Association) connector and RIC/UAC (Rapid Intervention Crew/Universal Air Connection) connector of the supply unit may be included to facilitate a connection with the source of compressed air through ensuring compatibility with the source of compressed air. The system may also include an isolation valve of the fill station to isolate a fill station from a remaining portion of the air distribution system.

The system may also include at least one of a fire rated material and a fire rated assembly to enclose the distribution structure such that the distribution structure has the ability to withstand elevated temperatures for a prescribed period of time. A selector valve that is accessible by an emergency personnel may be included to isolate the source of compressed air from the air storage sub-system such that the breathable air of the source of compressed air is directly deliverable to the air fill station through the piping distribution. In another aspect, a method includes ensuring that a prescribed pressure of an emergency support system maintains within a threshold range of the prescribed pressure by including a valve of the emergency support system to prevent leakage of breathable air from the emergency support system, safeguarding a filling process of a breathable air apparatus by enclosing the breathable air apparatus in a secure chamber of a fill site of the emergency support system of the tunnel structure to provide a safe placement to supply the breathable air to the breathable air apparatus, and providing a spare storage of breathable air through an air storage tank of a storage sub-system to store breathable air that is replenishable with a source of compressed air.

The method may also include preventing leakage of air from the emergency support system leading to a potential pressure loss of the emergency support system through utilizing a valve of any of the supply unit and the fill site and discontinuing transfer of breathable air from the source of compressed air to the emergency support system through utilizing a valve of the emergency support system. The method may also include automatically releasing breathable air from the emergency support system when the system pressure of the emergency support system exceeds the prescribed pressure through triggering a safety relief valve of any of the supply unit and the fill site, ensuring compatibility of the emergency support system and the source of compressed air of an authority agency through any of a CGA connector and a RIC/UAC connector of the supply unit. The method may also include adjusting a fill pressure to ensure that the fill pressure of the source of compressed air does not exceed the prescribed pressure of the emergency support system through a pressure regulator of the supply unit. The method may also include monitoring any of the system pressure of the emergency support system and the fill pressure of the source of compressed air through the pressure gauge of the supply unit enclosure.

BRIEF DESCRIPTION OF THE DRAWINGS

Example embodiments are illustrated by way of example and not limitation in the figures of the accompanying drawings, in which like references indicate similar elements and in which:

FIG. 4A is a front view of an supply unit, according to one embodiment.

FIG. 4B is a rear view of an supply unit, according to one embodiment.

DETAILED DESCRIPTION

Figure 1:
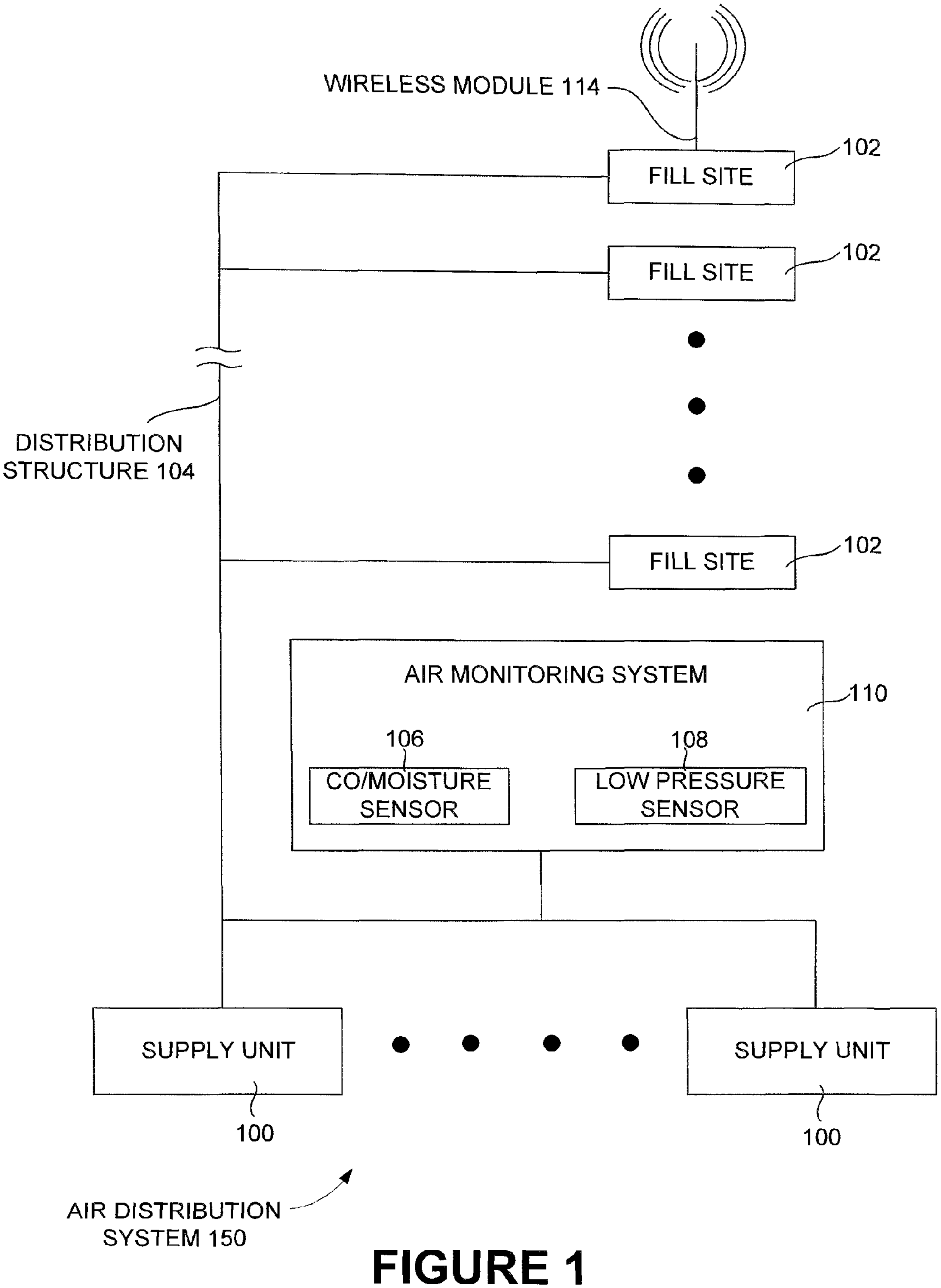
FIG. 1 is a diagram of an air distribution structure in a tunnel structure, according to one embodiment.

A safety system and method of a tunnel structure are disclosed. In the following description, for the purposes of explanation, numerous specific details are set forth in order to provide a thorough understanding of the various embodiments. It will be evident, however to one skilled in the art that the various embodiments may be practiced without these specific details.

A tunnel may be used for mining as passageways for trains, motor vehicles, diverting rivers around dam sites, housing underground installations such as power plants, and/or for conducting water. Ancient civilizations used tunnels to carry water for irrigation and drinking, and in the 22nd century BC the Babylonians built a tunnel for pedestrian traffic under the Euphrates River. The Romans built aqueduct tunnels through mountains by heating the rock face with fire and rapidly cooling it with water, causing the rock to crack. The introduction of gunpowder blasting in the 17th century marked a great advance in solid-rock excavation. For softer soils, excavation is accomplished using devices such as the tunneling mole, with its rotating wheel that continuously excavate material and loads it onto a conveyor belt. Railroad transportation in the 19th-20th century led to a tremendous expansion in the number and length of tunnels. Brick and stone were used for support in early tunnels, but in modern tunneling steel is generally used until a concrete lining can be installed. A common method of lining involves spraying shotcrete onto the tunnel crown immediately after excavation.

In addition, the tunnel may be for pedestrians and/or cyclists, for general road traffic, for motor vehicles, for rail traffic, and/or for a canal. Aqueducts may be constructed purely for carrying water for consumption, and/or for hydroelectric purposes or as sewers. Some tunnels may carry other services such as telecommunications cables. There are even tunnels designed as wildlife crossings for European badgers and other endangered species. Some secret tunnels have also been made as a method of entrance or escape from an area (e.g., Cu Chi Tunnels).

A pedestrian tunnel or other underpass beneath a road may be a subway. This term was also used in the past in the United States, but is now used to refer to underground rapid transit systems. In addition, a central part of a rapid transit network may be built in tunnels. To allow non-level crossings, some lines may be in deeper tunnels than others. At metro stations there may also be pedestrian tunnels from one platform to another. Often, ground-level railway stations may also have one or more pedestrian tunnels under the railway to enable passengers to reach the platforms without having to walk across the tracks. Tunnels may be dug in various types of materials, from soft clays to hard rocks, and the method of excavation may heavily depend on the ground conditions.

Cut-and-cover may be a method of construction for shallow tunnels where a trench is excavated and roofed over. In addition, strong supporting beams may be necessary to avoid the danger of the tunnel collapsing. For example, shallow tunnels may be of the cut-and-cover type (e.g., if under water of the immersed-tube type), while deep tunnels are excavated, often using a tunneling shield. For intermediate levels, both methods are possible.

Tunnel-boring machines (e.g., TBMs) can be used to automate the entire tunneling process. There are a variety of TBMs that can operate in a variety of conditions. One type of TBM, called an earth-pressure balance machine, can be used deep below the water table. This may pressurize the cutter head with either fluid or air in order to balance the water pressure. As a result operators of the TBM may go through decompression chambers, much like divers. One of the biggest TBM built was operated to drill the tunnel as part of the High Speed Rail-link South in the Netherlands. Its diameter is approximately 14.85 m.

The New Austrian Tunneling Method (NATM) was developed in the 1960s. The main idea of this method is to use the geological stress of the surrounding rock mass to stabilize the tunnel itself. Based on geotechnical measurements, an optimal cross section may be computed. The excavation is immediately protected by thin shotcrete, just behind the TBM. This creates a natural load-bearing ring, which may minimize the rock's deformation. By special monitoring, the NATM method may be relatively flexible, even at surprising changes of the geo-mechanical rock consistency during the tunneling work. The measured rock properties may lead to appropriate tools for tunnel strengthening.

Additionally, there are also some approaches to underwater tunnels, for instance an immersed tube as in Sydney Harbour. For water crossings, a tunnel may generally be more costly to construct than a bridge. However, navigational considerations may limit the use of high bridges or drawbridge spans when intersecting with shipping channels at some locations, necessitating use of a tunnel. Additionally, bridges may require a larger footprint on each shore than tunnels (e.g., in areas with particularly expensive real estate, such as Manhattan and urban Hong Kong), this is a strong factor in tunnels' favor. Boston's Big Dig project replaced elevated roadways with a tunnel system in order to increase traffic capacity, reclaim land, and reunite the city with the waterfront. Examples of water-crossing tunnels built instead of bridges include the Holland Tunnel and Lincoln Tunnel between New Jersey and Manhattan in New York City, and the Elizabeth River tunnels between Norfolk and Portsmouth, Va. and the Westerschelde tunnel, Zeeland, Netherlands. Other reasons for choosing a tunnel instead of a bridge may be aesthetic reasons (e.g., to preserve the above-ground view, landscape, and scenery), and also for weight capacity reasons (e.g., it may be more feasible to build a tunnel than a sufficiently strong bridge). Some water crossings may be a mixture of bridges and tunnels, such as the Denmark to Sweden link and the Chesapeake Bay Bridge-Tunnel in the eastern United States.

An underground city may include a network of tunnels that connect buildings, and may be located in the downtown area of a city. The network of tunnels may include office blocks, shopping malls, train stations, metro stations, theatres, and/or other attractions. An underground city may be accessed through the public space of any of the buildings connecting to it, and/or may have separate entries. The underground city may be especially important in cities with cold climates, as the downtown core may be enjoyed year round without regard to the weather. The underground city may be similar to skyway systems and may include some buildings linked by skyways or above-ground corridors rather than underground. An example of a famous underground city in the world is notably Montreal's.

In addition, Sydney has a series of underground shopping malls around one of the city's underground stations Town Hall. The network of tunnels runs south to the George Street cinema district, west under the town hall, and north to Pitt Street Mall through the Queen Victoria Building. The northern branch links Queen Victoria Building with Galleries Victoria, Sydney Central Plaza (which in turn links internally above ground to Westfield Centrepoint, Imperial Arcade, Skygarden, Glasshouse, and the MLC Centre). The linked centers run for over approximately 3 km. In 2005 Westfield corporation submitted a development application to link Sydney Central Plaza underground with 3 other properties on Pitt Street Mall and extend the tunnel network by a further 500 m.

In one embodiment, a safety system of a tunnel structure includes an supply unit (e.g., an supply unit 100 of FIGS. 1-3) of a tunnel structure to facilitate delivery of breathable air from a source of compressed air to an air distribution structure (e.g., an air distribution system 150,250,350 of FIGS. 1-3) of the tunnel structure, a valve (e.g., a check valve of a series of valves 410 of FIG. 4) to prevent a leakage of the breathable air from the air distribution structure (e.g., the air distribution system 150, 250, 350 of FIGS. 1-3) potentially leading to loss of a system pressure, a fill site (e.g., a fill site 102B of FIG. 6B, and/or a fill station 102A of FIG. 6A) interior to the tunnel structure to provide the breathable air to a breathable air apparatus at multiple locations of the tunnel structure, a distribution structure (e.g., a distribution structure 104 of FIGS. 1-3) that is compatible with use with compressed air that facilitates dissemination of the breathable air of the source of compressed air to multiple locations of the tunnel structure, In another embodiment, a method may include ensuring that a prescribed pressure of the emergency support system (e.g., the air distribution system 150,250,350 of FIGS. 1-3) maintains within a threshold range of the prescribed pressure by including a valve of the emergency support system to prevent leakage of breathable air from the emergency support system, safeguarding a filling process of a breathable air apparatus by enclosing the breathable air apparatus in a secure chamber of a fill site (e.g., a fill site 102B of FIG. 6B, and/or a fill station 102A of FIG. 6A) of the emergency support system of the tunnel structure to provide a safe placement to supply the breathable air to the breathable air apparatus, and/or providing a spare storage of breathable air through an air storage tank of a storage sub-system to store breathable air that is replenishable with a source of compressed air.

FIG. 1 is a diagram of an air distribution system 150 in a building structure, according to one embodiment. The air distribution system 150 may include any number of supply unit 100, any number of fill sites 102 (e.g., a fill panel and/or a fill station, etc.) that are coupled to the rest of the air distribution system 150 through a distribution structure 104. The air distribution system 150 may also include a air monitoring system 110 having a CO/Moisture sensor 106 and a pressure sensor 108. The supply unit 100 may be placed at a number of locations exterior to the building structure (e.g., a horizontal building structure such as a shopping mall, IKEA®, Home Depot®, a vertical building structure such as a high rise building, a mid rise building, and/or a low rise building, a mine, a subway, and/or a tunnel, etc.) to allow ease of access by a source of compressed air and/or to expedite supplying the air distribution system 150 with breathable air. The supply unit 100 may also be placed at locations that are substantially free of traffic (e.g., parked cars, vehicle movement, and/or human traffic, etc.) to decrease potential obstruction that may be present in an emergency situation (e.g., a building fire—a chemical attack, terror attack, subway accident, mine collapse, and/or a biological agent attack, etc.).

The fill sites 102 may also be placed at a number of locations of the building structure (e.g., a horizontal building structure such as a shopping mall, IKEA®, Home Depot®, a vertical building structure such as a high rise building, a mid rise building, and/or a low rise building, a mine, a subway, and/or a tunnel, etc.) to provide multiple access points to breathable air in the building structure. The building structure may have any number of fill sites 102 (e.g., a fill panel and/or a fill station, etc.) on each floor and/or have fill sites 102 (e.g., a fill panel and/or a fill station, etc.) on different floors. Each fill sites 102 may be sequentially coupled to one another and to the supply unit 100 through the distribution structure 104. The distribution structure 104 may include any number of pipes to expand an air carrying capacity of the air distribution system 150 such that breathable air may be replenished at a higher rate. In addition, the fill sites 102 may include wireless capabilities (e.g., a wireless module 114) for communication with remote entities (e.g., the supply unit 100, building administration, and/or an authority agency, etc.).

The air monitoring system 110 may contain multiple sensors such as the CO/moisture sensor 106 and the pressure sensor 108 to track air quality of the breathable air in the air distribution system 150. Since emergency personnel (e.g., a fire fighter, a SWAT team, a law enforcer, and/or a medical worker, etc.) depend on the breathable air distributed via the air distribution system 150, it is crucial that air quality of the breathable air be constantly maintained. The air monitoring system 110 may also include other sensors that detect other hazardous substances (e.g., benzene, acetamide, acrylic acid, asbestos, mercury, phosphorous, propylene oxide, etc.) that may contaminate the breathable air.

In one embodiment, the distribution structure 104 may be compatible with use with compressed air facilitates dissemination of the breathable air of the source of compressed air to multiple locations of the building structure. A fire rated material may encase the distribution structure 104 such that the distribution structure has the ability to withstand elevated temperatures for a period of time. The pipes of the distribution structure 104 may include a sleeve exterior to the fire rated material to further protect the fire rated material from any damage. Both ends of the sleeve may be fitted with a fire rated material that is approved by an authority agency. In addition, the distribution structure 104 may include a robust solid casing to prevent physical damage to the distribution structure potentially compromising the safety and integrity of the air distribution system.

The distribution structure 104 may include support structures at intervals no larger than five feet to provide adequate structural support for each pipe of the distribution structure 104. The pipes and the fittings of the distribution structure 104 may include any of a stainless steel and a thermoplastic material that is compatible for use with compressed air.

In another embodiment, the air distribution system may include an air monitoring system (e.g., the air monitoring system 110) to automatically track and record any impurities and contaminants in the breathable air of the air distribution system. The air monitoring system (e.g., the air monitoring system 110) may have an automatic shut down feature to suspend air distribution to the fill sites 102 in a case that any of an impurity and contaminant concentration exceeds a safety threshold. For example, a pressure monitoring system (e.g., the pressure sensor. 108) may automatically track and record the system pressure of the air distribution system. Further, a pressure switch may be electrically coupled to a alarm system such that the fire alarm system is set off when the system pressure of the air distribution system is outside a safety range.

Figure 2:
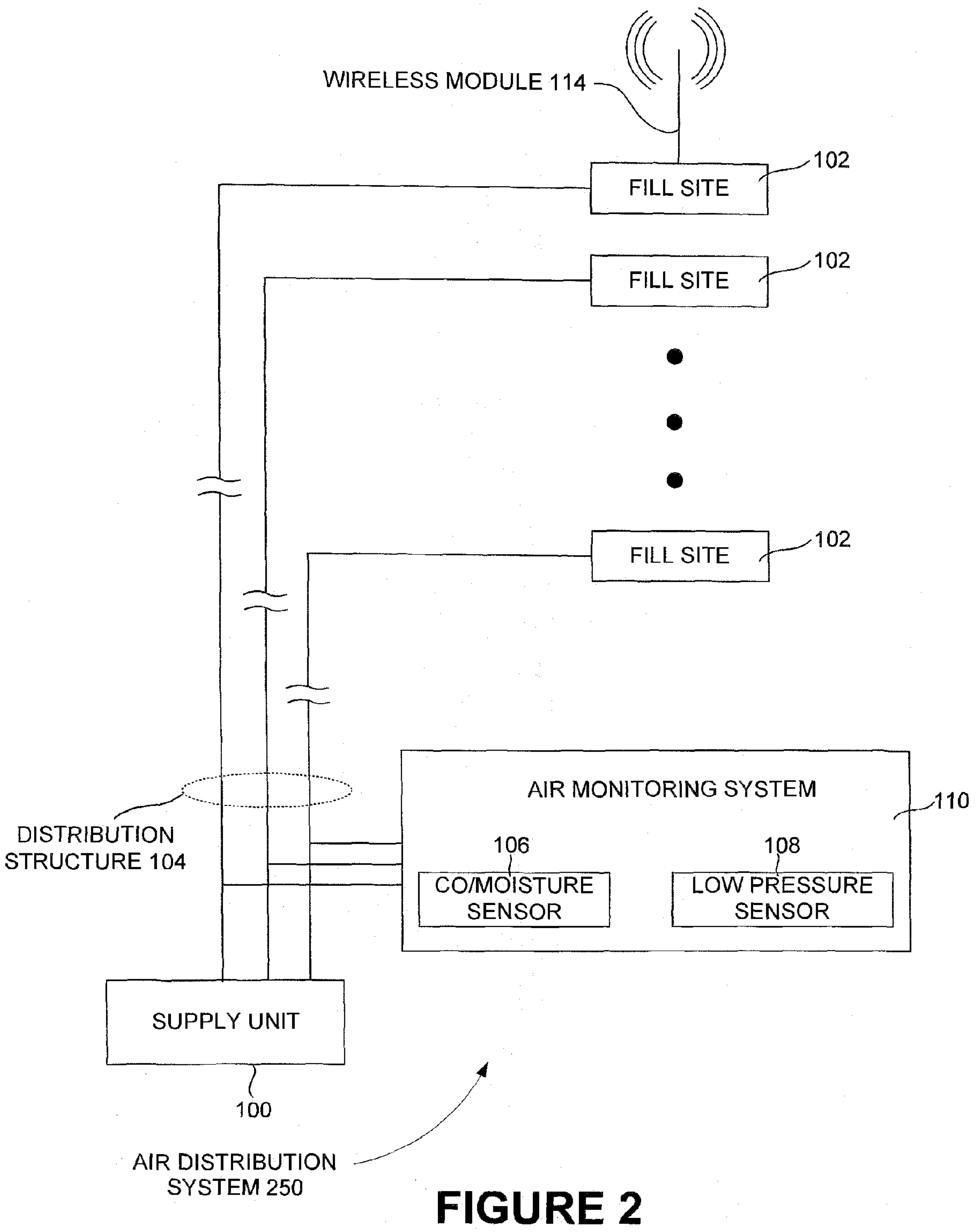
FIG. 2 is another diagram of an air distribution structure in a tunnel structure, according to one embodiment.

FIG. 2 is another diagram of an air distribution system 250 in a building structure, according to one embodiment. The air distribution system 250 may include any number of supply unit 100, any number of fill sites 102 (e.g., a fill panel and/or a fill station, etc.) that are coupled to the rest of the air distribution system 150 through a distribution structure 104. The air distribution system 150 may also include a air monitoring system 110 having a CO/Moisture sensor 106 and a pressure sensor 108. In the air distribution system 250, the distribution structure 104 may individually couple each fill sites 102 (e.g., a fill panel and/or a fill station, etc.) to a supply unit 100. Individual coupling may be advantageous in that in the case one pipe of the distribution structure 104 becomes inoperable the other pipes can still deliver air to the fill sites 102 (e.g., a fill panel and/or a fill station, etc.). The other system components (e.g., the fill sites 102, the supply unit 100, and the air monitoring system 110 were described in detail in the previous section).

Figure 3:
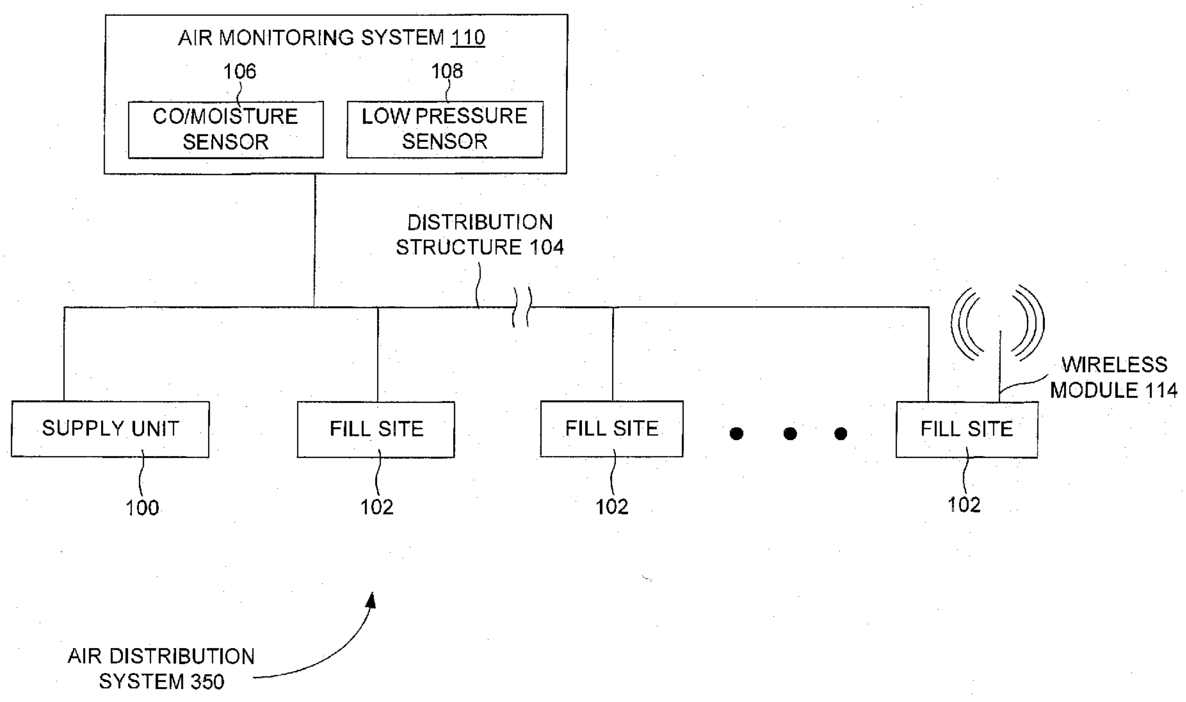
FIG. 3 is a diagram of an air distribution structure in a tunnel structure having fill sites located horizontally from one another, according to one embodiment.

FIG. 3 is a diagram of an air distribution system 350 in a building structure having fill sites 102 (e.g., a fill panel and/or a fill station, etc.) located horizontally from one another, according to one embodiment.

The air distribution system 350 may include any number of supply unit 100, any number of fill sites 102 (e.g., a fill panel and/or a fill station, etc.) that are coupled to the rest of the air distribution system 150 through a distribution structure 104. The air distribution system 150 may also include a air monitoring system 110 having a CO/Moisture sensor 106 and a pressure sensor 108. In the air distribution system 250, the distribution structure 104 may sequentially couple each fill site 102 (e.g., a fill panel and/or a fill station, etc.) displaced predominantly horizontally from a supply unit 100. Each air distribution system (e.g., the air distribution system 150, 250, 350) may be used in conjunction with one another depending on the particular architectural style of the building structure in a manner that provides most efficient access to the breathable air of the air distribution system reliably. The other system components (e.g., the fill site 102, the supply unit 100, and the air monitoring system 110 were described in detail in the previous section).

FIG. 4A is a front view of a supply unit 100, according to one embodiment.

The supply unit 100 provides accessibility of a source of compressed air to supply air to an air distribution system (e.g., an air distribution system 150, 250, and/or 350). The supply unit may include a fill pressure indicator 400, a fill control knob 402, a system pressure indicator 404, and/or a connector 406. The fill pressure indicator 400 may indicate the pressure level at which breathable air is being delivered by the source of compressed air to the air distribution system (e.g., an air distribution system 150, 250, and/or 350 of FIGS. 1-3). The system pressure indicator 404 may indicate the current pressure level of the breathable air in the air distribution system. The fill control knob 402 may be used to control the fill pressure such that the fill pressure does not exceed a safety threshold that the air distribution system is designed for. The connector 406 may be a CGA connector that is compatible with an air outlet of the source of compressed air of various emergency agencies (e.g., fire station, law enforcement agency, medical provider, and/or SWAT team, etc.). The connector 406 (e.g., CGA connector) of the supply unit 100 may facilitate a connection with the source of compressed air through ensuring compatibility of the supply unit 100 with the source of compressed air.

The supply unit 100 may include an adjustable pressure regulator of the supply unit 100 that is used to adjust a fill pressure of the source of compressed air to ensure that the fill pressure does not exceed the design pressure of the air distribution system. Further, the supply unit may also include at least one pressure gauge of the supply unit enclosure to indicate any of the system pressure (e.g., the system pressure indicator 404) of the air distribution system and the fill pressure (e.g., the fill pressure indicator 400) of the source of compressed air.

FIG. 4B is a rear view of a supply unit 100, according to one embodiment.

The supply unit also includes a series of valves 41 0 (e.g., a valve, an isolation valve, and/or a safety relief valve, etc.) to further ensure that system pressure is maintained within a safety threshold of the design pressure of the air distribution system.

The supply unit 100 of a building structure may facilitate delivery of breathable air from a source of compressed air to an air distribution system of the building structure. The supply unit 100 includes the series of valves 410 (e.g., the valve, and/or the safety relief valve, etc.) to prevent a leakage of the breathable air from the air distribution system potentially leading to loss of a system pressure. For example, the supply unit 100 may include the valve of the series of valves 410 to automatically suspend transfer of breathable air from the source of compressed air to the air distribution system when useful. The safety relief valve of the supply unit 100 and/or the fill site 102 may release breathable air when a system pressure of the air distribution system exceeds a threshold value beyond the design pressure to ensure reliability of the air distribution system through maintaining the system pressure such that it is within a pressure rating of each component of the air distribution system.

Figure 5:
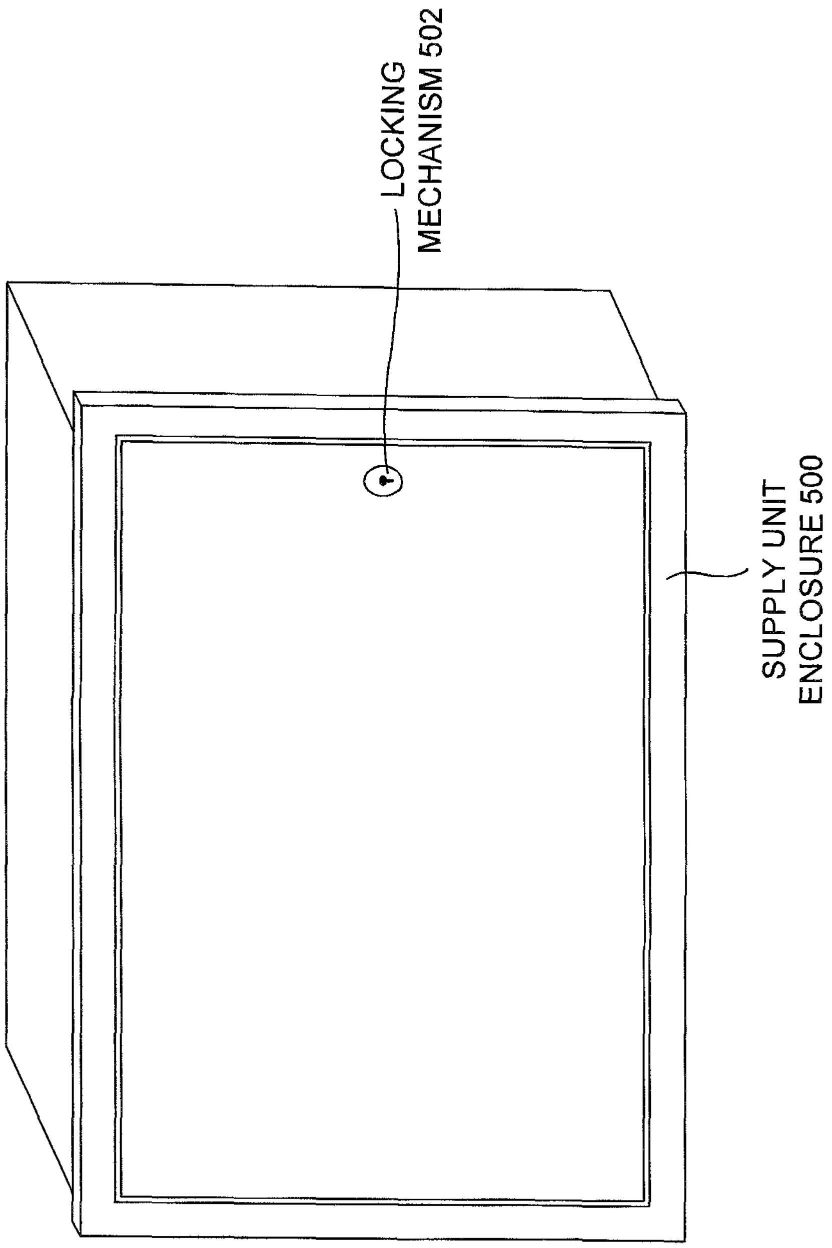
FIG. 5 is an illustration of an supply unit enclosure, according to one embodiment.

FIG. 5 is an illustration of a supply unit enclosure 500, according to one embodiment.

The supply unit enclosure 500 may include a locking mechanism 502 to secure the supply unit 100 from unauthorized access. Further, the supply unit enclosure 500 may also contain fire rated material such that the supply unit 100 is able to withstand burning elevated temperatures.

The supply unit enclosure 500 encompassing the supply unit 100 may have any of a weather resistant feature, ultraviolet and infrared solar radiation resistant feature to prevent corrosion and physical damage. The locking mechanism 502 may secure the supply unit from intrusions that potentially compromise safety and reliability of the air distribution system. In addition, the supply unit enclosure 500 may include a robust metallic material of the supply unit enclosure 500 to minimize a physical damage due to various hazards to protect the supply unit 100 from any of an intrusion and damage. The robust metallic material may be at least substantially 18 gauge carbon steel. The supply unit enclosure 500 may include a visible marking to provide luminescence in a reduced light environment. The locking mechanism 502 may also include a tamper switch such that a alarm is automatically triggered and a signal is electrically coupled to any of a relevant administrative personnel of the building structure and the emergency supervising station when an intrusion of any of the supply unit and the secure chamber occurs.

Figure 6A:
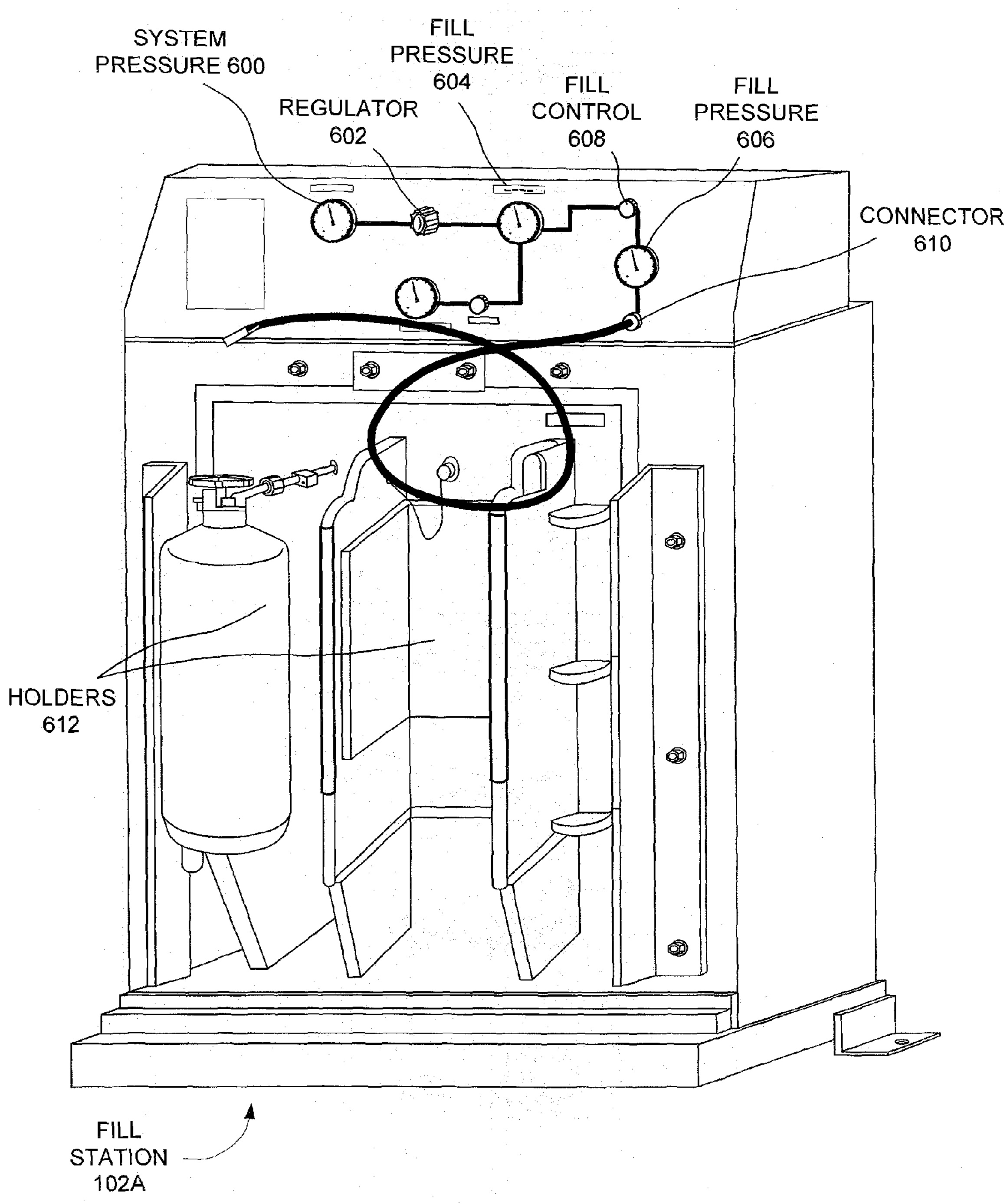
FIG. 6A is an illustration of a fill station, according to one embodiment.

FIG. 6A is an illustration of a fill station 102A, according to one embodiment.

The fill station 102A may be a type of fill site 102 of FIG. 1. The fill station 102A may include a system pressure indicator 600, a regulator 602, a fill pressure indicator 604, another fill pressure indicator 606, and/or fill control knob 608. The fill station 102A may also include a RIC/UAC connector 610 and multiple breathable air apparatus holders 612 used to supply air from the air distribution system. The fill pressure indicator 604 may indicate the pressure level at which breathable air is being delivered by the source of compressed air to the air distribution system (e.g., an air distribution system 150,250, and/or 350 of FIGS. 1-3). The system pressure indicator 600 may indicate the current pressure level of the breathable air in the air distribution system. The fill control knob 608 may be used to control the fill pressure such that the fill pressure does not exceed a safety threshold that the air distribution system is designed for. The RIC/UAC connector 610 may facilitate direct coupling to emergency equipment to supply breathable air through a hose that is connected to the RIC/UAC connector 610. In essence, precious time may be saved because the emergency personnel may not need to spend the time to remove the emergency equipment from their rescue attire before they can be supplied with breathable air. Further, the RIC/UAC connector 610 may also directly couple to a face-piece of a respirator to supply breathable air.

The multiple breathable air apparatus holders 612 can hold multiple compressed air cylinders to be filled simultaneously. In addition, the multiple breathable air apparatus holders 612 can be rotated such that additional compressed air cylinders may be loaded while the multiple compressed air cylinders are filled inside the fill station 102A. The fill station 102A may be a rupture containment chamber such that over pressurized compressed air cylinders are shielded and contained to prevent injuries.

In one embodiment, the fill station 102A interior to the building structure may provide the breathable air to a breathable air apparatus at multiple locations of the building structure. A secure chamber of the fill station 102A may be a safety shield that confines a possible rupture of an over-pressurized breathable air apparatus within the secure chamber. The fill station 102A may include a valve to prevent leakage of air from the air distribution system potentially leading to pressure loss of the air distribution system through ensuring that the system pressure is maintained within a threshold range of the design pressure to reliably fill the breathable air apparatus. An isolation valve may be included to isolate a breathable fill station from a remaining portion of the air distribution system.

The isolation valve may be automatically actuated based on an air pressure sensor of the air distribution system. The fill station 102A may include at least one pressure regulator to adjust a fill pressure to fill the breathable air apparatus and to ensure that the fill pressure does not exceed the pressure rating of the breathable air apparatus potentially resulting in a rupture of the breathable air apparatus. The fill station 102A may include at least one pressure gauge to indicate any of a fill pressure (e.g., the fill pressure indicator 604, 606) of the fill station and a system pressure (e.g., the system pressure indicator 600) of the air distribution system. In one embodiment, the fill station 102A may have a physical capacity to enclose at least one breathable air apparatus and may include a RIC/UAC connector to facilitate a filling of the breathable air apparatus. The fill station may also include a securing mechanism of the secure chamber of the fill station having a locking function is automatically actuated via a coupling mechanism with a flow switch that indicates a status of air flow to the breathable air apparatus that is fillable in the fill station.

Figure 6B:
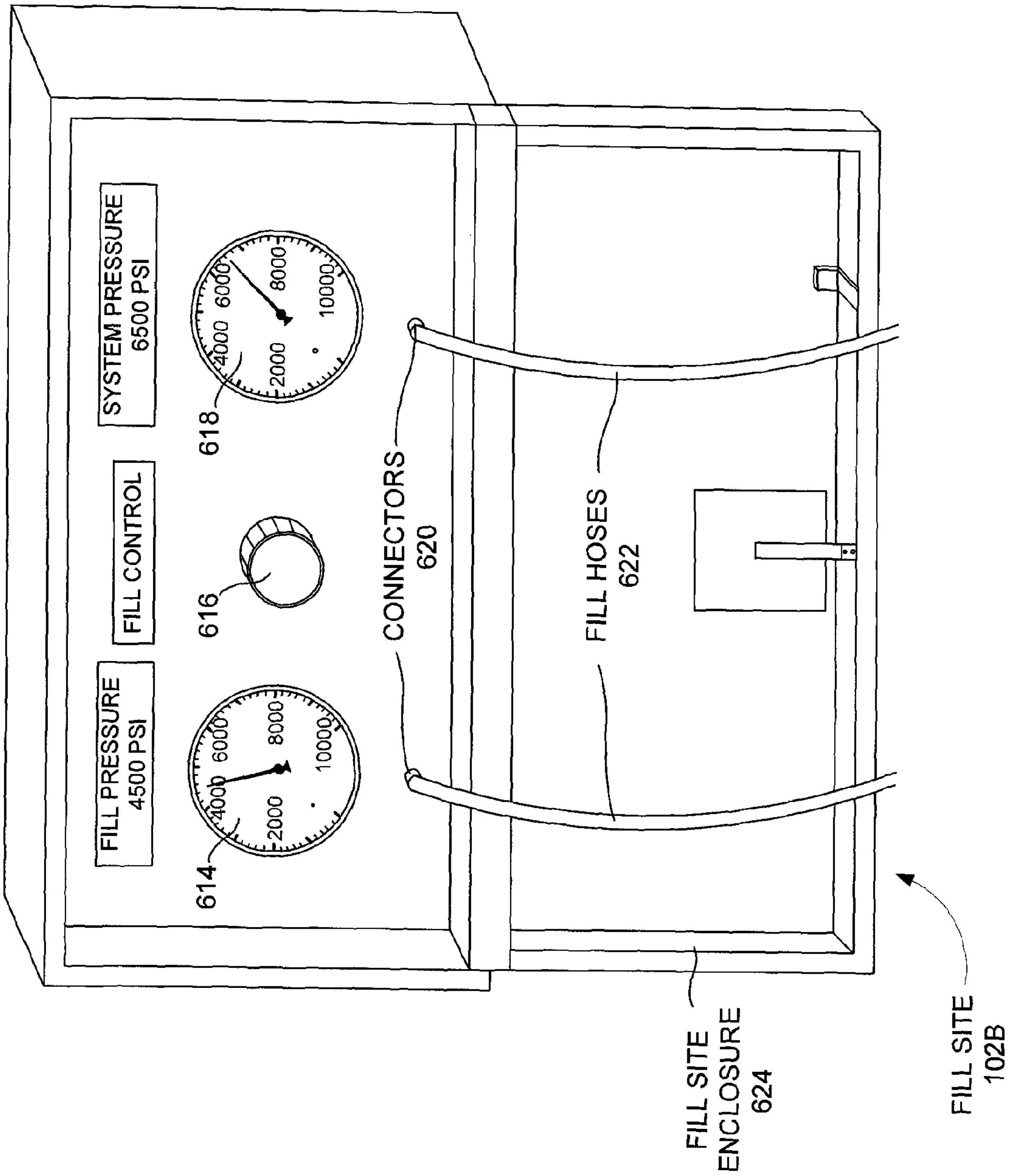
FIG. 6B is an illustration of a fill site, according to one embodiment.

FIG. 6B is an illustration of a fill site 102B, according to one embodiment.

The fill site 102B (e.g., a fill panel) includes a fill pressure indicator 614 (e.g., pressure gauge), a fill control knob 616 (e.g., pressure regulator), a system pressure indicator 618, a number of connector 620 (e.g., a RIC/UAC connector), and/or fill hoses 622. The fill site 102B may also include a locking mechanism of a fill site enclosure 624 (e.g., a fill panel enclosure) to secure the fill site 102B from intrusions that potentially compromise safety and reliability of the air distribution system. The system pressure indicator 618 may indicate the current pressure level of the breathable air in the air distribution system. The fill control knob 616 (e.g., pressure regulator) may be used to adjust the fill pressure such that the fill pressure does not exceed a safety threshold that the air distribution system is designed for.

The connector 620 may facilitate direct coupling to emergency equipment to supply breathable air through a hose that is connected to the connector 620. In essence, precious time may be saved because the emergency personnel may not need to spend the time to remove the emergency equipment from their rescue attire before they can be supplied with breathable air. Further, the connector 620 connected with the fill hoses 622 may also directly couple to a face-piece of a respirator to supply breathable air to either emergency personnel (e.g., a fire fighter, a SWAT team, a law enforcer, and/or a medical worker, etc.) and/or stranded survivors in need of breathing assistance. Each of the fill hoses 622 may have different pressure rating of the fill site 102B is couple-able to any of a self-contained breathable air apparatus and respiratory mask having a compatible RIC/UAC connector. The fill panel enclosure may include a visible marking to provide luminescence in a reduced light environment.

The fill site 102B interior to the building structure may have the connector 620 (e.g., the RIC/UAC connector) to fill a breathable air apparatus to expedite a breathable air extraction process from the air distribution system and to provide the breathable air to the breathable air apparatus at multiple locations of the building structure. The fill site 102B may include a safety relief valve set to have an open pressure of at most approximately 10% more than a design pressure of the air distribution system to ensure reliability of the air distribution system through maintaining the system pressure such that it is within a threshold range of a pressure rating of each component of the air distribution system. The fill site enclosure 624 may comprise of at least 18 gauge carbon steel to minimize physical damage of various naturally occurring and man-imposed hazards through protecting the fill panel from any of an intrusion and damage. The fill site 102B may include an isolation valve to isolate a damaged fill panel from a remaining operable portion of the air distribution system.

Figure 7A:
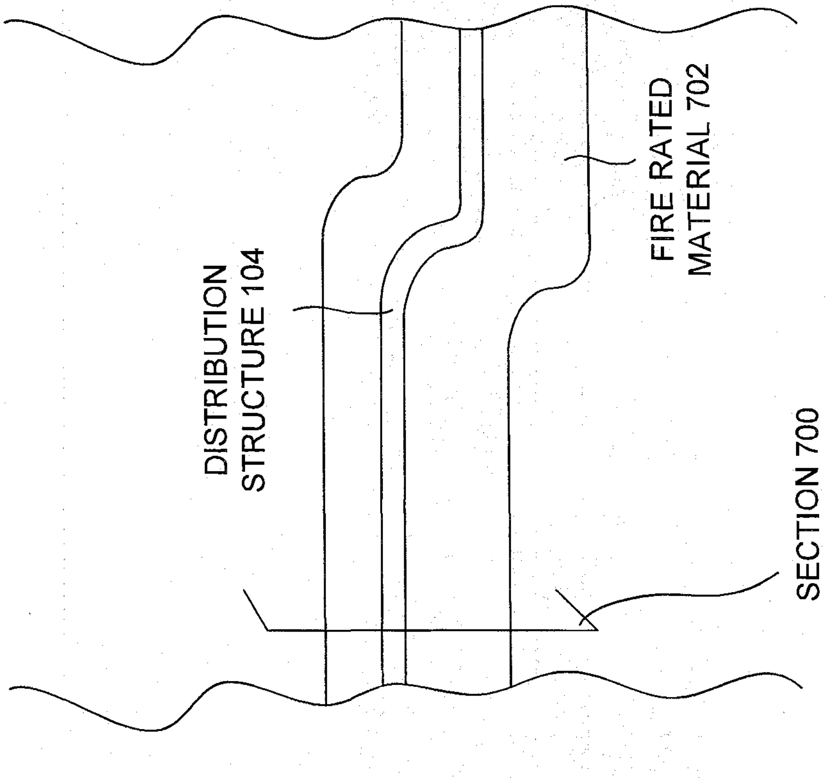
FIG. 7A is a diagrammatic view of a pipe of a distribution structure embedded in a fire rated material, according to one embodiment.

FIG. 7A is a diagrammatic view of a distribution structure 104 embedded in a fire rated material, according to one embodiment.

The distribution structure 104 may be enclosed in the fire rated material 702. The fire rated material may prevent the distribution structure 104.from damage in a fire such that an air distribution system (e.g., the air distribution system 150, 250,350 of FIGS. 1-3) may be operational for a longer time period in an emergency situation (e.g., a building fire, a chemical attack, terror attack, subway accident, mine collapse, and/or a biological agent attack, etc.). Section 700 is a cross section of the distribution structure 104 embedded in the fire rated material 702.

Figure 7B:
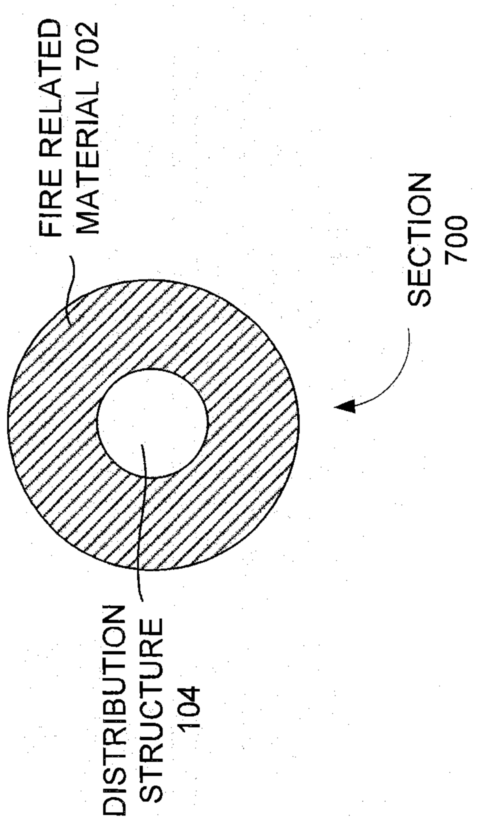
FIG. 7B is a cross sectional view of a pipe of a distribution structure embedded in a fire rated material, according to one embodiment.

FIG. 7B is a cross sectional view 700 of a distribution structure embedded in a fire rated material, according to one embodiment.

Section 700 is a cross section of the distribution structure 104 embedded in the fire rated material 702.

Figure 8:
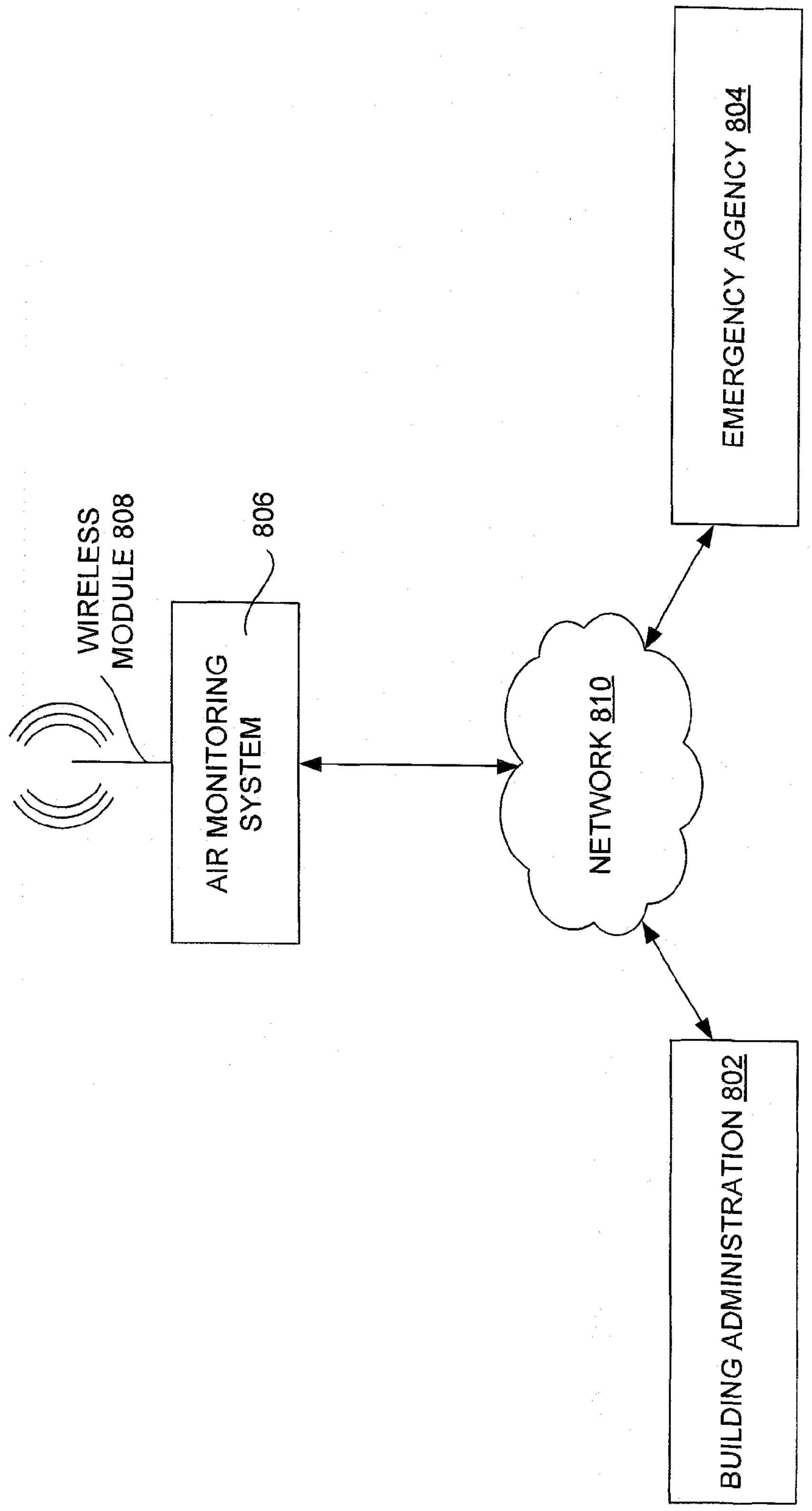
FIG. 8 is a network view of a air monitoring system that communicates building administration and an emergency agency, according to one embodiment.

FIG. 8 is a network view of a air monitoring system 806 with a wireless module 808 that communicates with building administration 802 and an authority agency 804 through a network 810, according to one embodiment.

The air monitoring system 806 may include various sensors (e.g., CO/moisture sensor 106 of FIG. 1, pressure sensor 108 of FIG. 1, and/or hazardous substance sensor, etc.) and/or status indicators regarding system readiness information (e.g., system pressure, in use, not in use, operational status, fill site usage status, fill site operational status, etc.). The air monitoring system 806 may communicate sensor readings to a building administration 802 (e.g., building management, security, and/or custodial services, etc.) such that proper maintenance measures may be taken. The air monitoring system 806 may also send alerting signals as a reminder for regular system inspection and maintenance to the building administration 802 through the network 810. The air monitoring system 806 may also communicate sensor readings to an authority agency 804 (e.g., a police station, a fire station, and/or a hospital, etc.).

Figure 9:
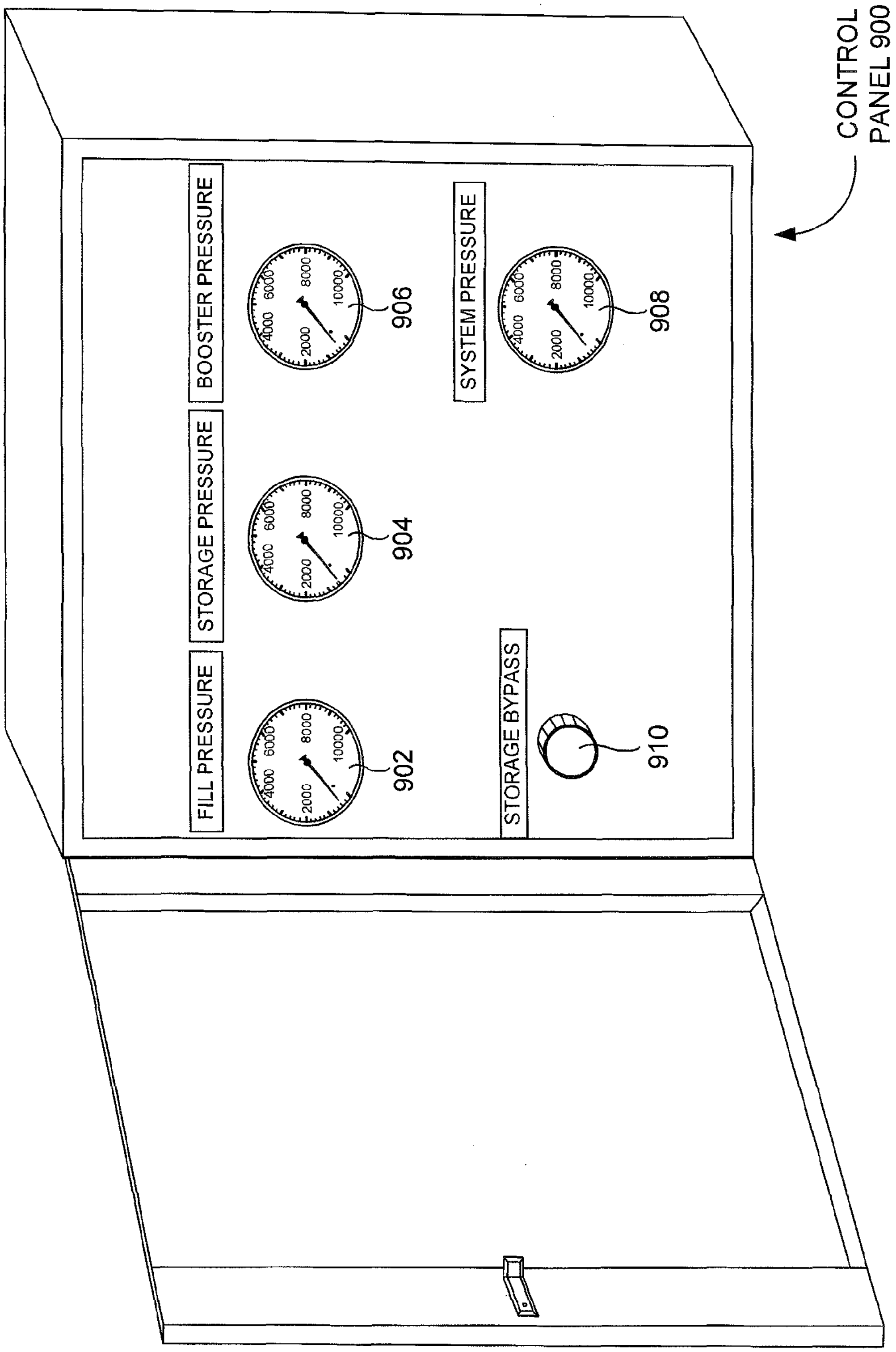
FIG. 9 is a front view of a control panel of an air storage sub-system, according to one embodiment

FIG. 9 is a front view of a control panel 900 of a air storage sub-system 1050, according to one embodiment.

The control panel 900 includes a fill pressure indicator 902, a storage pressure indicator 904, a booster pressure indicator 906, a system pressure indicator 908 and/or a storage bypass 910. The fill pressure indicator 902 may indicate the pressure level at which breathable air is being delivered by the source of compressed air to the air distribution system (e.g., an air distribution system 150,250, and/or 350 of FIGS. 1-3). The storage pressure indicator 904 may display the pressure level of air storage tanks in the air storage sub-system 1050. The booster pressure indicator may display the pressure level of a booster cylinder. The system pressure indicator 908 may indicate the current pressure level of the breathable air in the air distribution system. Air may be directly supplied to the air distribution system (e.g., an air distribution system 150,250, and/or 350 of FIGS. 1-3) through the storage bypass 910.

Figure 10:
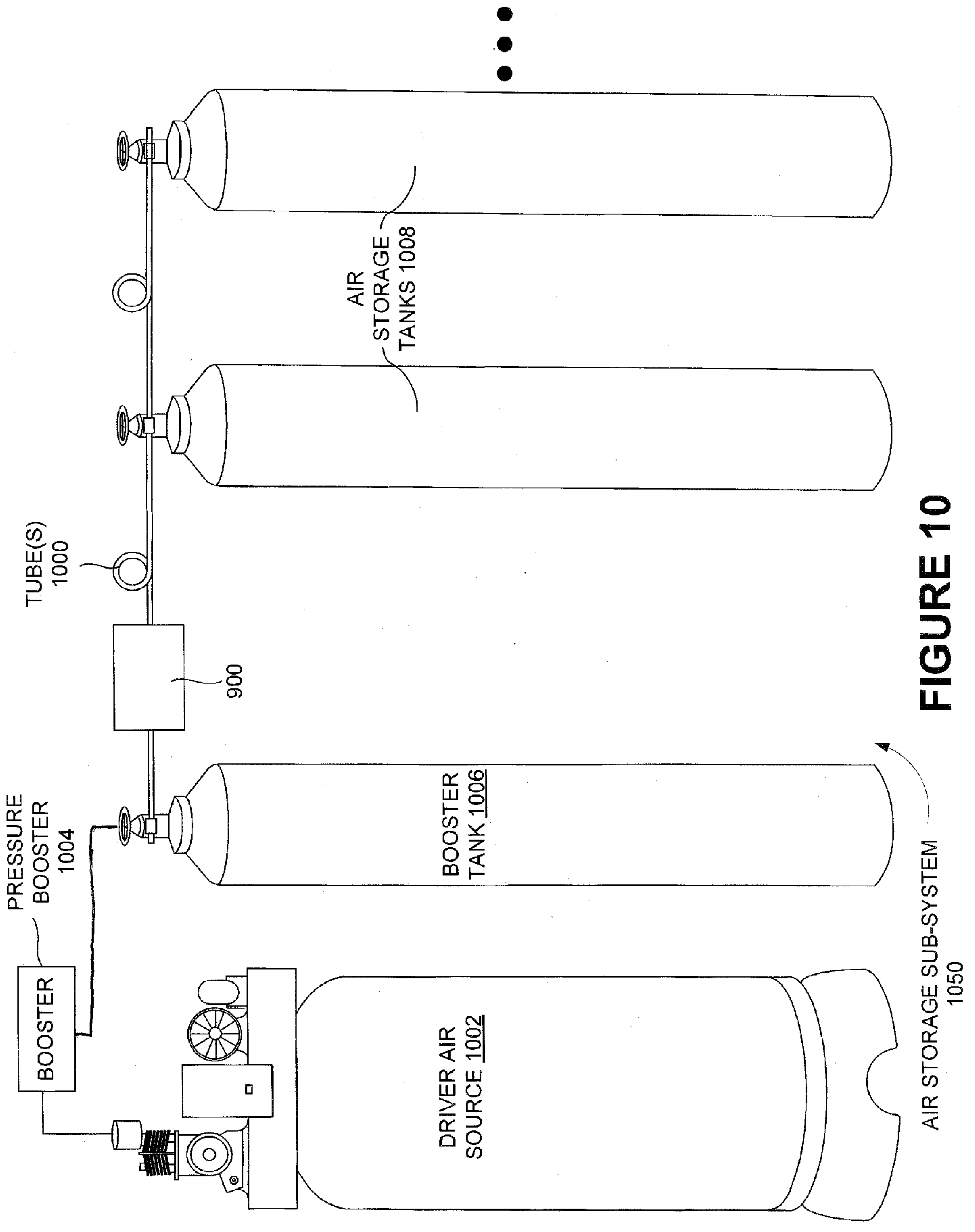
FIG. 10 is an illustration of an air storage sub-system, according to one embodiment.

FIG. 10 is an illustration of a air storage sub-system 1050, according to one embodiment.

The air storage sub-system 1050 may include a control panel 900, tubes 1000, a driver air source 1002, a pressure booster 1004, a booster tank 1006, and/or any number of air storage tanks 1008. The control panel 900 may provide status information regarding the various components of the air storage sub-system 1050. The tubes 1000 may couple each air storage tank 1008 to one another in a looped configuration to increase robustness of the tubes 1000. The driver air source 1002 may be used to pneumatically drive the pressure booster 1004 to maintain a higher pressure of the air distribution system such that a breathable air apparatus is reliably filled. The booster tank 1006 may store air at a higher pressure than the air stored in the air storage tanks 1008 to ensure that the air distribution system can be supplied with air that is sufficiently pressurized to fill a breathable air apparatus.

In one embodiment, the air storage sub-system 1050 may include an air storage tank 1008 to provide a storage of air that is dispersible to multiple locations of the building structure. The number of air storage tanks 1008 of the air storage sub-system 1050 may be coupled to each other through tubes 1000 having a looped configuration to increase robustness of the tubes 1000 through preventing breakage due to stress. In addition, a booster tank (e.g., the booster tank 1006) of the air storage sub-system 1050 may be coupled to the plurality of air storage tanks to store compressed air of a higher pressure than the compressed air that is stored in the air storage tank 1008. A driver air source 1002 of the air storage sub-system 1050 may be coupled to a pressure booster (e.g., the pressure booster 1004) to pneumatically drive a piston of the pressure booster (e.g., the pressure booster 1004) to maintain a higher pressure of the air distribution system such that a breathable air apparatus is reliably filled.

Further, the driving air source may enable the breathable air to be optimally supplied to the building structure through allowing the breathable air to be isolated from driving the pressure booster 1004. The air storage sub-system 1050 may also include an air monitoring system (e.g., the carbon monoxide sensor and moisture sensor 106 of FIGS. 1-3) to automatically track and record any of impurities and contaminants in the breathable air of the air distribution system. The air monitoring system 110 of FIGS. 1-3 may include an automatic shut down feature to suspend air dissemination to the fill stations (e.g., the fill station 102A of FIG. 6A) in a case that any of impurity levels and contaminant level exceed a safety threshold. The air storage sub-system 1050 may also include a pressure monitoring system (e.g., a pressure sensor 108 of FIG. 1) to continuously track and record the system pressure of the air distribution system (e.g., the air distribution system 150,250,350 of FIGS. 1-3). In addition, a pressure switch may be electrically coupled to an alarm system such that the alarm system is set off when the system pressure of the air distribution system (e.g., the air distribution system 150,250, 350 of FIGS. 1-3) is outside a safety range. The pressure switch (e.g., a pressure sensor 108 of FIG. 1) may electrically transmit a warning signal to an emergency supervising station when the system pressure of the air distribution system (e.g., the air distribution system 150,250,350 of FIGS. 1-3) is below the prescribed level.

The air storage sub-system 1050 may include at least one indicator unit to provide status information of the air distribution system (e.g., the air distribution system 150, 250, 350 of FIGS. 1-3) including storage pressure, booster pressure, pressure of the compressed air source, and the system pressure. Further, the air storage sub-system 1050 may also include a selector valve that is accessible by an emergency personnel to isolate the source of compressed air from the air storage sub-system such that the breathable air of the source of compressed air is directly deliverable to the fill site (e.g., the fill site 102B of FIG. 6B, and/or the fill station 102A of FIG. 6A) through the distribution structure. The air storage sub-system 1050 may be housed in a fire rated enclosure that is certified to be rupture containable to withstand elevated temperatures for a period of time.

Figure 11:
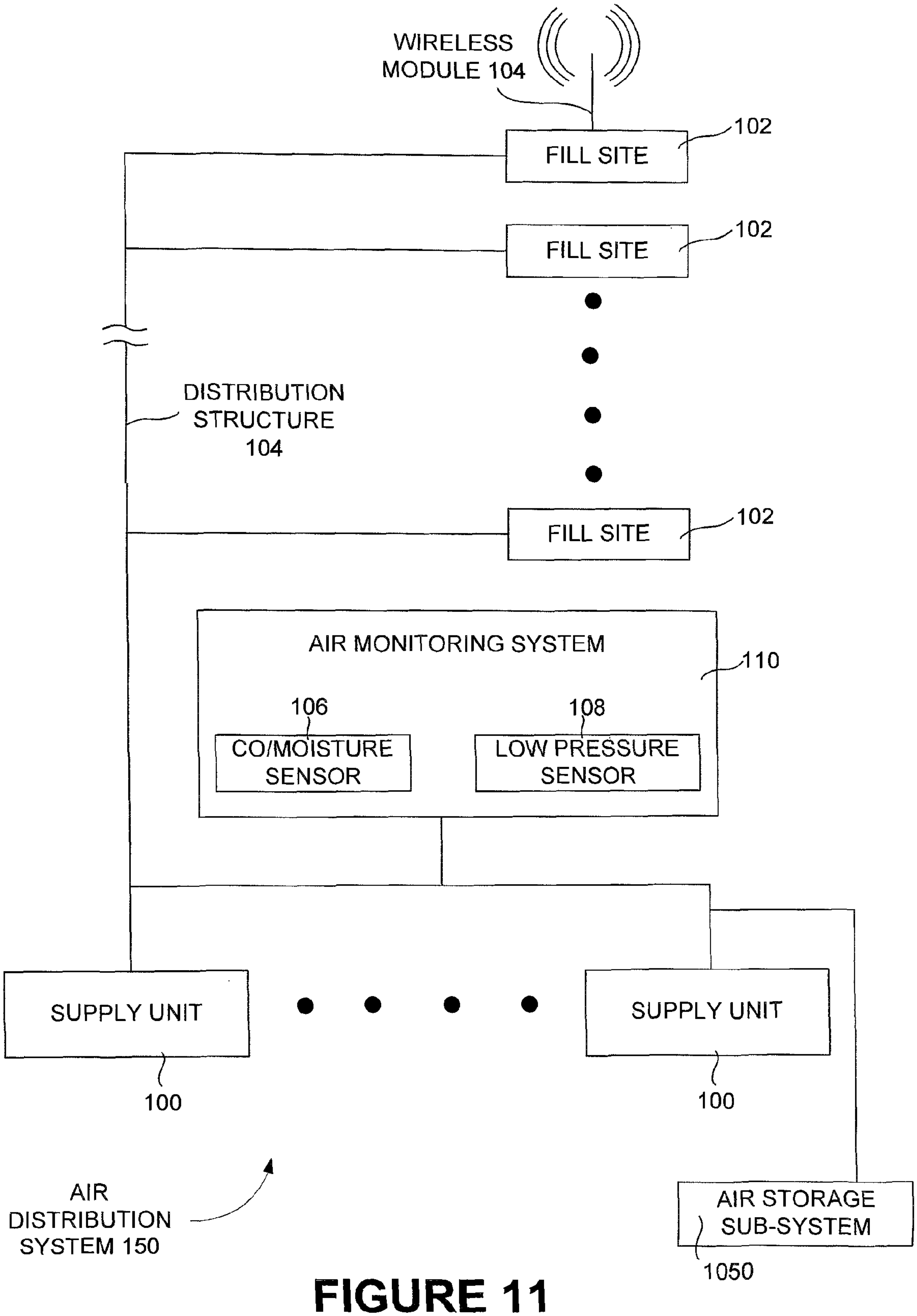
FIG. 11 is a diagram of an air distribution structure having an air storage subsystem, according to one embodiment.

FIG. 11 is a diagram of an air distribution system having a air storage subsystem 1050, according to one embodiment.

The air distribution system 150 may include any number of supply unit 100, any number of fill sites (e.g., the fill site 102B of FIG. 6B, and/or the fill station 102A of FIG. 6A) that are coupled to the rest of the air distribution system 150 through a distribution structure 104. The air distribution system 150 may also include an air monitoring system 110 having a CO/Moisture sensor 106 and a pressure sensor 108, and/or the air storage sub-system 1050. The air storage sub-system 1050 is as previously described. Air storage tanks 1008 and/or a booster tank 1006 of the air storage subsystem 1050 of FIG. 10 may be supplied with breathable air through a source of compressed air that is coupled to the air distribution system through the supply unit 100 and/or supplied independently of the supply unit 100. The air storage sub-system 1050 may provide a spare source of breathable air to the air distribution system (e.g., the air distribution system 150,250,350 of FIGS. 1-3) in addition to an external source of compressed air.

Figure 12:
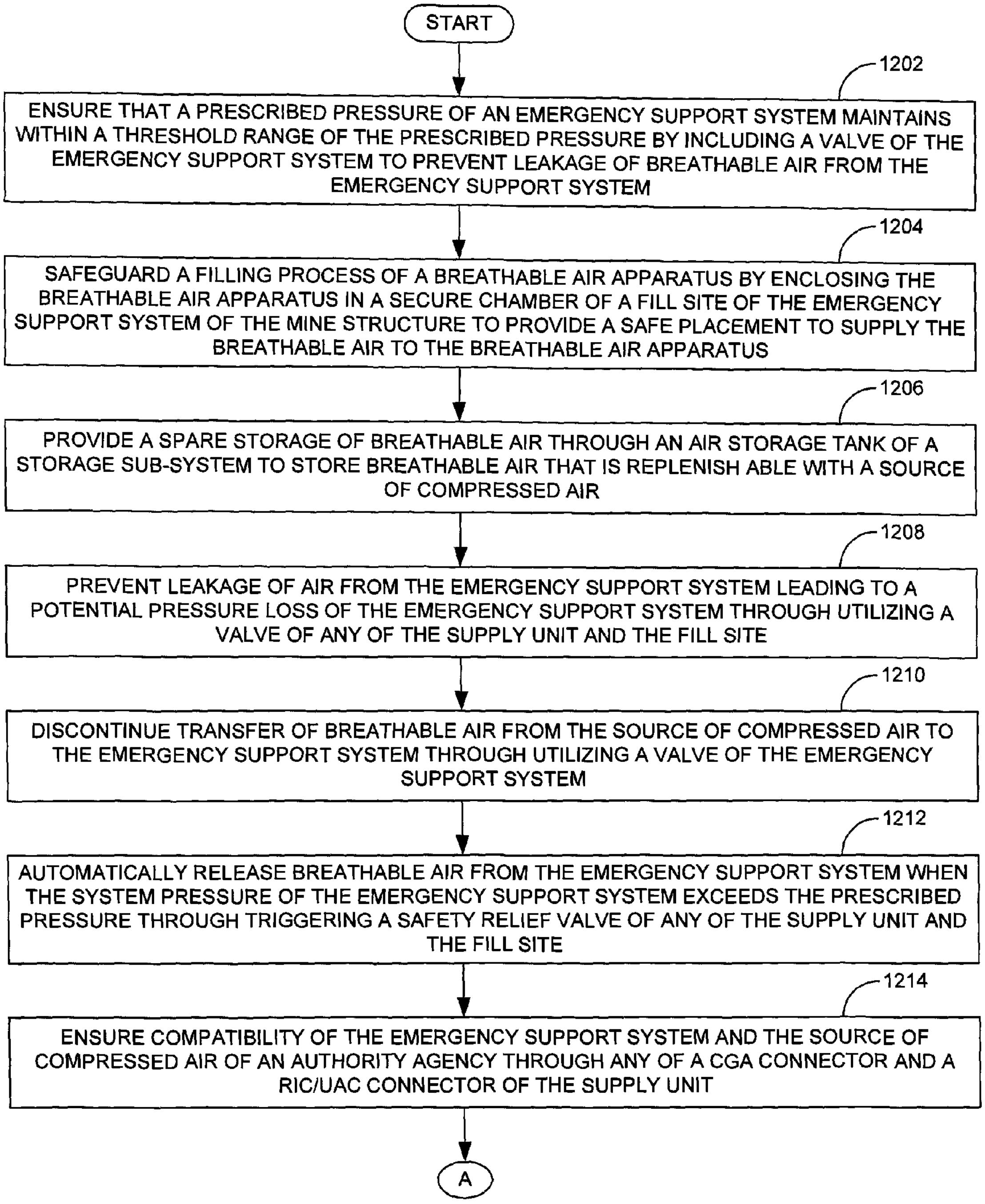
FIG. 12 is a process flow of a safety of a tunnel structure, according to one embodiment.

FIG. 12 is a process flow of a safety of a tunnel structure, according to one embodiment. In operation 1202, a prescribed pressure of an emergency support system (e.g., the air distribution system 150,250,350 of FIGS. 1-3) maintains within a threshold range of the prescribed pressure may be ensured by including a valve of the emergency support system (e.g., the air distribution system 150,250,350 of FIGS. 1-3) to prevent leakage of breathable air from the emergency support system (e.g., the air distribution system 150,250,350 of FIGS. 1-3). In operation 1204, a filling process of a breathable air apparatus may be safeguarded by enclosing the breathable air apparatus in a secure chamber of a fill site of the emergency support system (e.g., the air distribution system 150,250,350 of FIGS. 1-3) of the tunnel structure to provide a safe placement to supply the breathable air to the breathable air apparatus.

In operation 1206, a spare storage of breathable air may be provided through an air storage tank of a storage sub-system to store breathable air that is replenishable with a source of compressed air. In operation 1208, leakage of air from the emergency support system (e.g., the air distribution system 150,250,350 of FIGS. 1-3) leading to a potential pressure loss of the emergency support system (e.g., the air distribution system 150,250,350 of FIGS. 1-3) may be prevented through utilizing a valve (e.g., a check valve of a series of valves 410 of FIG. 4) of any of the supply unit (e.g., the supply unit 100 of FIGS. 1-3) and the fill site. In operation 1210, transfer of breathable air from the source of compressed to the emergency support system (e.g., the air distribution system 150, 250,350 of FIGS. 1-3) may be discontinued through utilizing a valve (e.g., a check valve of a series of valves 410 of FIG. 4) of the emergency support system (e.g., the air distribution system 150,250,350 of FIGS. 1-3).

In operation 1212, breathable air may be automatically released from the emergency support system (e.g., the air distribution system 150, 250, 350 of FIGS. 1-3) when the system pressure of the emergency support system (e.g., the air distribution system 150, 250, 350 of FIGS. 1-3) exceeds the prescribed pressure through triggering a safety relief valve (e.g., a check valve of a series of valves 410 of FIG. 4) of any of the supply unit (e.g., the supply unit 100 of FIGS. 1-3) and the fill site. In operation 1214, compatibility of the emergency support system (e.g., the air distribution system 150, 250, 350 of FIGS. 1-3) and the source of compressed air of an authority agency may be ensured through any of a CGA connector (e.g., the connector 406 (e.g., CGA connector) of FIG. 4B) and a RIC/UAC connector of the supply unit (e.g., the supply unit 100 of FIGS. 1-3.

Figure 13:
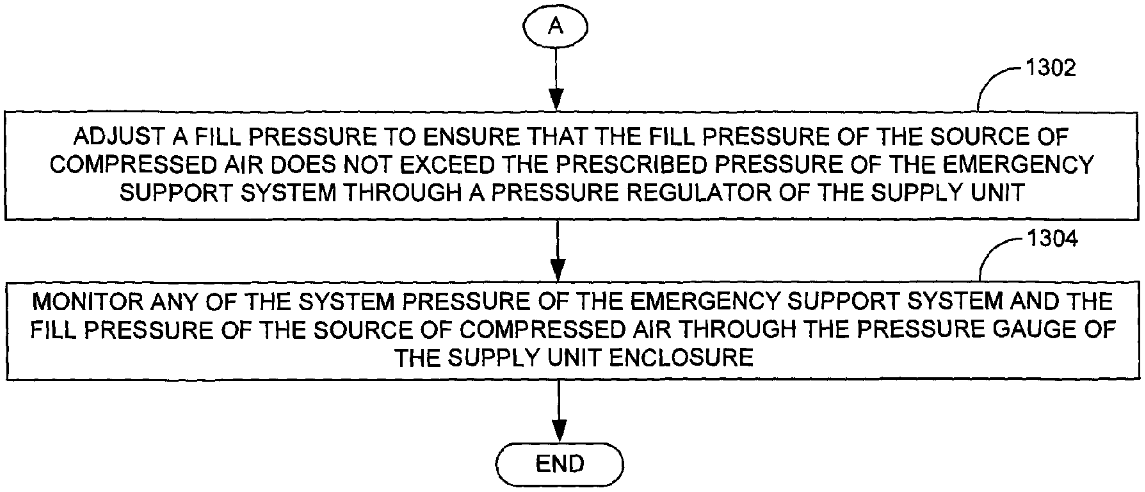
FIG. 13 is a process flow that describes further the operations of FIG. 12, according to one embodiment.

FIG. 13 is a process diagram that describes further the operations of FIG. 12, according to one embodiment. In operation 1302, a fill pressure may be adjusted to ensure that the fill pressure of the source of compressed air does not exceed the prescribed pressure of the emergency support system (e.g., the air distribution system 150,250,350 of FIGS. 1-3) through a pressure regulator of the supply unit (e.g., the supply unit 100 of FIGS. 1-3). In operation 1304, any of the system pressure of the emergency support system (e.g., the air distribution system 150,250,350 of FIGS. 1-3) and the fill pressure of the source of compressed air may be monitored through the pressure gauge of the supply unit enclosure (e.g., the supply unit enclosure 500 of FIG. 5).

In an embodiment, a safety system of a structure may include a fill site system in the tunnel structure. A fill site system may include an apparatus that allows one or more firefighters to simultaneously refill an air tank of a Self Contained Breathing Apparatus (SCBA) unit while continuing to operate their breathing apparatus through the use of a specialized air connection (e.g., a rapid intervention company/crew (RIC) universal air connection (UAC), also described as the RIC/UAC coupling). The fill station may be a site (e.g., a location of a structure, a location within a building, etc.) in the tunnel structure to fill (e.g., supply, build up a level of, occupy the whole of, spread throughout, complete) a container with breathable air (e.g., compressed atmospheric gas meeting firefighting safety standards for quality and/or filtration) for emergency use. The specialized air connection may include a quick-connect system that allows the user to attach and/or detach the coupling without the use of a threaded connection.

In contrast, other methods and/or structures to refill an air tank of a SCBA unit may require a wearer to disconnect the air tank from the SCBA apparatus, connect the air tank to a mechanism to deliver compressed air into the air tank, and reinstall the air tank in the SCBA unit through a series of time consuming steps, during which the wearer of the SCBA unit may not have access to breathable air. The steps may involve screwing a connection together and unscrewing the connection using multiple turning actions. By allowing the wearer to continue to breathe while refilling an air tank of the SCBA unit, the wearer may avoid breathing excessive amounts of toxic, superheated and/or otherwise unbreathable air that may lead to immediate injury, long term health risks, unconsciousness, disablement, cancer, and/or death.

A SCBA unit may be a device worn by rescue workers, firefighters, industrial workers, and others to provide breathable air in a hostile environment. Areas in which the SCBA may be used for industrial purposes may include mining, petrochemical, chemical, and nuclear industries. The SCBA units designed for firefighting use may include components chosen for heat and flame resistance, which may add to a cost of manufacturing. Lighter materials may also be chosen to reduce the amount of effort needed by a firefighter to use the apparatus.

An open-circuit rescue or the firefighter SCBA may include a full-face mask, regulator, air cylinder, cylinder pressure gauge, and a harness with adjustable shoulder straps and waist belt that allows it be worn on a user's back. Air cylinders for the SCBA may be made of aluminium, steel, and/or of a composite construction (e.g., carbon-fiber wrapped). The composite cylinders may be the lightest in weight, which may make them preferred by fire departments. However, they may also have the shortest lifespan out of various types of air cylinders, and they may be taken out of service after 15 years. Air cylinders may further be required to undergo hydrostatic testing (e.g., every 3 years for composite cylinders, every 5 years for metal cylinders). The air cylinder may come in one of three standard sizes: 30, 45 or 60 minutes of breathing time. The relative fitness, and the level of exertion of the wearer, may often result in a variation of the actual usable time that the SCBA can provide air. Working time during which a firefighter is not exposed to toxic gasses may be reduced by 25% to 50% based on these factors.

The SCBA may use a negative and/or positive pressure system to deliver breathable air. A "negative pressure" SCBA may be used with a standard face mask instead of filter canisters, and air may be delivered when the wearer breathes in, or in other words, reduces the pressure in the mask to less than external air pressure. One disadvantage of this method may be that any leaks in the device or the interface between the mask and the face of the wearer could result in a reduction of the protection offered by the SCBA. The wearer may inhale small and/or large quantities of polluted and/or toxic gas through such leaks. A "positive pressure" SCBA may be set to maintain a small positive pressure inside a face mask. Although the pressure may drop when the wearer inhales, the positive pressure SCBA may continue to maintain a higher positive pressure than external air pressure within the mask. The positive pressure may cause any leak in the mask to result, the device always maintains a higher pressure inside the mask than outside of the mask. Thus, even if the mask leaks slightly, there may be a flow of clean air out of the device that prevents inward leakage of external air.

Some potential sources of a leak in the SCBA system may be hair that prevents a complete seal of a face mask, an overly large size of a face mask, a face mask wrinkle, a face mask puncture and/or tear, a degraded seal between face mask components. Other causes of a leak may include a temporary dislocation of the face mask, such as through an accidental collision with another firefighter and/or a wall, a fall by a fatigued and/or disoriented wearer, or falling debris and/or structural components of a burning building. A wearer of the face mask may also enter a darkened building where electrical power has failed and/or been interrupted or where smoke makes it difficult for the wearer to see, which may contribute to accidental collisions. A face mask may further be dislodged by a building occupant being assisted by a firefighter.

The use of a specialized air connection (e.g., a RIC/UAC fitting and/or coupling) may allow an SCBA unit user to avoid a risk associated with breathing toxic gasses while an air cylinder is refilled by filling the SCBA unit cylinder while it is still connected to the SCBA unit as an operational source of breathable air. The RIC/UAC fitting connected to the fill site 102 may therefore assist with expediting a breathable air extraction process from the air distribution system. The use of the specialized air connection may also avoid a risk of dislodging a user's mask and creating leaks in the SCBA system while the wearer refills an air cylinder. The specialized air connection may be a fitting designed to allow a direct transfer of air between fire fighters as a means of providing breathable air to a fire fighter without access to another means of refilling an air tank of an SCBA unit. The specialized air connection may further allow a fire fighter to provide air to a downed and/or disabled fire fighter who is unable to refill his own air tank. The specialized air connection may be a RIC/UAC coupling. The RIC/UAC coupling may allow two fire fighters with SCBA units to share their air regardless of manufacturer, after which the firefighters may have approximately equal levels of air. When a firefighter uses the RIC/UAC coupling to connect to another firefighter's SCBA unit, the pressure levels for each are balanced as air from an SCBA unit with more air flows to the connected SCBA unit.

A manufacturer of an SCBA unit may be required by the National Fire Protection Association (NFPA) 1981, the Standard on Open-Circuit Self-Contained Breathing Apparatus (SCBA) for Emergency Services, to build SCBA units that contain a RIC/UAC connection. The RIC/UAC coupling may be required for a newly manufactured SCBA unit to be in compliance for firefighting. The NFPA may be a U.S. organization that creates and maintains minimum standards and requirements for fire prevention and suppression activities, training, and equipment, as well as other life-safety codes and standards. This may include everything from building codes to the personal protective equipment utilized by firefighters while extinguishing a fire. State, local, and national governments may incorporate the standards and codes developed by the Association into their own law either directly or with only minor modifications. Even when not written into law, the Association's standards and codes may be accepted and recognized as a professional standard by a court of law.

NFPA 1981 may state in part that the RIC/UAC connection should allow a fully charged breathing air cylinder to connect to an SCBA unit of an entrapped and/or downed firefighter. The RIC/UAC coupling may be used in conjunction with a high pressure line. NFPA 1981 may further state that the pressurized air source should be able to provide 100 liters of air per minute using a RIC/UAC female fitting at a pressure compatible with the SCBA being used at an incident. The NFPA 1981 may also state that, for newly manufactured SCBA, the universal connection (RIC/UAC) should be permanently fixed to the unit within four inches of the threads of the SCBA cylinder valve.

The fill site 102 system may include variety of components to assist with expediting a breathable air extraction process from the air distribution system. For example, the fill site 102 system may include the supply unit 100 of a building structure to facilitate delivery of breathable air from a source of compressed air to the air distribution system 150 of the building structure. The fill site 102 may further include a valve to prevent leakage of the breathable air from the air distribution system 150 potentially leading to loss of system pressure. The fill site 102 system may further include a fill panel interior to the building structure having a RIC/UAC fitting pressure rated for a fill outlet of the fill panel to fill a breathable air apparatus to expedite a breathable air extraction process from the air distribution system 150 and to provide the breathable air to the breathable air apparatus at multiple locations of the building structure. The system may further include a distribution structure that is compatible with use with compressed air that facilitates dissemination of the breathable air of the source of compressed air to multiple locations of the building structure.

The valve to prevent leakage of the breathable air from the air distribution system 150 may be a part attached to a pipe and/or tube that controls the flow of a gas and/or a liquid. The valve may isolate the fill site 102 from the remainder of the fill site 102 system by preventing pressurized air from reaching the pressure gauge and the RIC/UAC fitting. Isolating the RIC/UAC fitting and pressure gauge may protect the parts from wear and/or possible damage due to fluctuating air pressures within the system. In addition, in the event of damage to and/or malfunction of the RIC/UAC fitting, pressure gauge and/or other connected parts, the valve may prevent the remainder of the system from venting gas through the damaged and/or malfunctioning part. The valve may be controlled by the turning knob placed in proximity to the pressure gauge to facilitate a control of the fill site 102 station by a firefighter under hazardous conditions. Some potential causes of damage to the fill site 102 may include a fire hazard, building damage, through a malfunction of a fire fighter's mating connection and/or SCBA unit.

In one or more embodiments, the fill panel (e.g., a control panel of the fill site, a flat, vertical, area where control and/or monitoring instruments are displayed) may include gauges to monitor system air pressure and fill pressure (e.g., as illustrated in FIG. 6). The valve to prevent leakage of the breathable air from the air distribution system 150 may be controlled by a knob mounted on the fill panel. The fill panel may include a hose that is connected to the RIC/UAC fitting (e.g., the fill hoses 622). The RIC/UAC fitting may be pressure rated (e.g., rated to 3000 psi, 4500 psi, etc.) for a fill outlet of the fill panel to fill a breathable air apparatus (e.g., a SCBA unit air cylinder, a SCUBA tank, etc.). The pressure rating may allow the RIC/UAC fitting to operate up to the rated pressure within a safety factor (e.g., 1.5, a multiple of the rated pressure) up to which the RIC/UAC fitting is designed and/or certified to operate.

As described above, the RIC/UAC fitting may expedite a breathable air extraction process from the air distribution system 150 and to provide the breathable air to the breathable air apparatus. The expedited breathable air extraction process may take place at multiple locations of the building structure (e.g., different floors, hallways, near emergency exits, etc.). These locations may be near typical points where fire fighters and emergency workers may encounter while searching a building that is on fire. These locations may also be near emergency exits where building occupants are likely to pass by on their way out of a building, where they may obtain access to breathable air either directly or with the assistance of a fire fighter.

In one or more embodiments, the system may further include a distribution structure that is compatible with use with compressed air that facilitates dissemination of the breathable air of the source of compressed air to multiple locations of the building structure. The distribution structure may include piping, pressure valves, and/or controls to regulate and/or direct pressurized air.

In one or more embodiments, the system may include the supply unit enclosure 500 that includes a weather resistant feature (e.g., to prevent lightning, wind, rain, and/or flooding damage, etc.). The system may include a supply unit enclosure 500 to prevent corrosion and/or physical damage (e.g., power surges in electronic components) caused by ultraviolet, infrared, and/or other types of solar radiation (e.g., using a metallic shield, using lead, and/or a chemical coating). The system may further include the locking mechanism 502 of the supply unit enclosure 500 (e.g., to prevent tampering, vandalism, and/or thieves.)

In one or more embodiments, the system may further include a fill panel enclosure (e.g., the fill site enclosure 624) to secure the fill panel from intrusions (e.g., due to falling building components, collisions with building occupants, etc.) that potentially compromise safety and reliability of the air distribution system. The supply unit enclosure 500 may be comprised of 18 gauge carbon steel that minimizes physical damage due to various hazards by protecting the supply unit 100 from intrusion and/or damage due to vehicle collisions, flooding, acid rain, snow, etc.

In one or more embodiments, the system may further include a valve of the supply unit 100 to perform any of a suspension of transfer and a reduction of flow of breathable air from the source of compressed air to the air distribution system 150 when useful. The valve of the supply unit 100 may therefore reduce a supply of air (e.g., an air pressure) to the distribution system when an excess pressure is provided by an external compressed air source. The valve of the supply unit 100 may cut off an incoming air supply that fails to meet required purity standards for fire fighters. The valve may also reduce an incoming air supply that is being vented through a leak and/or malfunctioning valve of the system to prevent a waste of a compressed air source.

In one or more embodiments, the system may further include a safety relief valve of any of the supply unit 100 and the fill panel set to have an open pressure of at most approximately 10% more than a design pressure of the air distribution system 150 to ensure reliability of the air distribution system through maintaining the system pressure such that it is within a threshold range of a pressure rating of each component of the air distribution system 150. The safety valve may prevent an overfilling of an air cylinder beyond its rated pressure capacity, which may cause the air cylinder to rupture. The safety valve may prevent a compressed air source from delivering air to hoses and/or fittings designed for lower pressures. The safety valve may prevent a rupture and/or other damage within the air delivery system caused by a spike in pressure. Some potential causes of a pressure spike may include a malfunctioning and/or improper pressure source, changes in temperature, and/or an explosion.

In one or more embodiments, the system may further include any Compressed Gas Association (CGA) connector and/or the RIC/UAC connector to ensure compatibility and to facilitate a connection of the supply unit 100 with a source of compressed air.

Although the present embodiments have been described with reference to specific example embodiments, it will be evident that various modifications and changes may be made to these embodiments without departing from the broader spirit and scope of the various embodiments. For example, the various devices, modules, analyzers, generators, etc. described herein may be enabled and operated using hardware circuitry (e.g., CMOS based logic circuitry), firmware, software and/or any combination of hardware, firmware, and/or software (e.g., embodied in a machine readable medium). For example, the various electrical structure and methods may be embodied using transistors, logic gates, and electrical circuits (e.g., application specific integrated ASIC circuitry).

In addition, it will be appreciated that the various operations, processes, and methods disclosed herein may be embodied in a machine-readable medium and/or a machine accessible medium compatible with a data processing system (e.g., a computer system), and may be performed in any order. Accordingly, the specification and drawings are to be regarded in an illustrative rather than a restrictive sense.

The invention claimed is:

1. A safety system of a tunnel structure, comprising:

a supply unit of a tunnel structure to facilitate delivery of breathable air from a source of compressed air to an air distribution system of the tunnel structure;

a valve to prevent leakage of the breathable air from the air distribution system potentially leading to loss of system pressure;

a fill site interior to the tunnel structure to provide the breathable air to a breathable air apparatus at multiple locations of the tunnel structure;

a distribution structure that is compatible with use with compressed air that facilitates dissemination of the breathable air of the source of compressed air to multiple locations of the tunnel structure; and an air monitoring system to automatically track and record any of impurities and contaminants in the breathable air of the air distribution system.

2. The system of claim 1 further comprising a secure chamber of the fill station as a safety shield that confines a possible rupture of an over-pressurized breathable air apparatus within the secure chamber.

3. The system of claim 1 further comprising an air storage sub-system to provide an additional supply of air to the tunnel structure in addition to the source of compressed air.

4. The system of claim 3 further comprising an air storage tank of the air storage sub-system to provide storage of air that is dispersible to multiple locations of the tunnel structure.

5. The system of claim 3 further comprising a booster tank of the air storage subsystem coupled to the air storage tank to store compressed air of a higher pressure than the compressed air that is stored in the air storage tank.

6. The system of claim 3 further comprising a driving air source of the air storage sub-system to pneumatically drive a piston of a pressure booster to maintain a higher pressure of the air distribution system such that a breathable air apparatus is reliably filled.

7. The system of claim 1 wherein the air monitoring system includes an automatic shut down feature to suspend air dissemination to the tunnel structure in a case that any of impurity levels and contaminant levels exceed a safety threshold.

8. The system of claim 1 further comprising a pressure monitoring system to continuously track and record the system pressure of the air distribution system.

9. The system of claim 1 further comprising any of a CGA (Compressed Gas Association) connector and RIC/UAC (Rapid Intervention Crew/Universal Air Connection) connector of the supply unit to facilitate a connection with the source of compressed air through ensuring compatibility with the source of compressed air.

10. The system of claim 1 further comprising an isolation valve of the fill station to isolate a fill station from a remaining portion of the air distribution system.

11. The system of claim 1 further comprising at least one of a fire rated material and a fire rated assembly to enclose the distribution structure such that the distribution structure has the ability to withstand elevated temperatures for a prescribed period of time.

12. The system of claim of claim 1 further comprising a selector valve that is accessible by an emergency personnel to isolate the source of compressed air from the air storage sub-system such that the breathable air of the source of compressed air is directly deliverable to the air fill station through the distribution structure.

13. A method of safety of a tunnel structure, comprising:

ensuring that a prescribed pressure of an emergency support system maintains within a threshold range of the prescribed pressure by including a valve of the emergency support system to prevent leakage of breathable air from the emergency support system;

safeguarding a filling process of a breathable air apparatus by enclosing the breathable air apparatus in a secure chamber of a fill site of the emergency support system of the tunnel structure to provide a safe placement to supply the breathable air to the breathable air apparatus;

providing a spare storage of breathable air through an air storage tank of a storage sub-system to store breathable air that is replenishable with a source of compressed air; and monitoring the breathable air of the air distribution system to automatically track and record any of impurities and contaminants therein.

14. The method of claim 13 further comprising preventing leakage of air from the emergency support system leading to a potential pressure loss of the emergency support system through utilizing a valve of any of the supply unit and the fill site.

15. The method of claim 14 further comprising discontinuing transfer of breathable air from the source of compressed air to the emergency support system through utilizing a valve of the emergency support system.

16. The method of claim 13 further comprising automatically releasing breathable air from the emergency support system when the system pressure of the emergency support system exceeds the prescribed pressure through triggering a safety relief valve of any of the supply unit and the fill site.

17. The method of claim 13 further comprising ensuring compatibility of the emergency support system and the source of compressed air of an authority agency through any of a CGA (Compressed Gas Association) connector and a RIC/UAC (Rapid Intervention Crew/Universal Air Connection) connector of the supply unit.

18. The method of claim 13 further comprising adjusting a fill pressure to ensure that the fill pressure of the source of compressed air does not exceed the prescribed pressure of the emergency support system through a pressure regulator of the supply unit.

19. The method of claim 18 further comprising monitoring any of the system pressure of the emergency support system and the fill pressure of the source of compressed air through the pressure gauge of the supply unit enclosure.

* * * * *